(12) United States Patent
Zollinger et al.

(10) Patent No.: US 12,740,771 B2
(45) Date of Patent: Sep. 22, 2026

(54) WASTE COLLECTION CART FOR COLLECTING WASTE DURING A MEDICAL PROCEDURE

(71) Applicant: Stryker Corporation, Kalamazoo, MI (US)

(72) Inventors: Michael Zollinger, Chelsea, MI (US); Jacob C. Foor, Kalamazoo, MI (US); Chamara L. Gamhewage, Kalamazoo, MI (US); Brian MacLachlan, Norton Shores, MI (US); Peter LaDuke, Holland, MI (US); Rachel Wallace, Monona, WI (US); Michael Hammond, Monona, WI (US); Fernando Erismann, Sacramento, CA (US); Brooke Mason, Mattawan, MI (US); Noah Needler, Mattawan, MI (US); Michael Peterson, Richland, MI (US); Caitlynn Roy, Portage, MI (US); Grant Westphal, Delton, MI (US)

(73) Assignee: Stryker Corporation, Portage, MI (US)

( * ) Notice: Subject to any disclaimer, the term of this patent is extended or adjusted under 35 U.S.C. 154(b) by 506 days.

(21) Appl. No.: 17/602,020

(22) PCT Filed: Apr. 11, 2020

(86) PCT No.: PCT/US2020/027850

§ 371 (c)(1),
(2) Date: Oct. 7, 2021

(87) PCT Pub. No.: WO2020/210763

PCT Pub. Date: Oct. 15, 2020

(65) Prior Publication Data

US 2022/0142621 A1 May 12, 2022

Related U.S. Application Data

(60) Provisional application No. 62/849,548, filed on May 17, 2019, provisional application No. 62/833,399, filed on Apr. 12, 2019.

(51) Int. Cl.
*A61B 50/13* (2016.01)
*A61B 10/00* (2006.01)
(Continued)

(52) U.S. Cl.
CPC ...... *A61B 10/0096* (2013.01); *A61B 10/0045* (2013.01); *A61B 10/04* (2013.01);
(Continued)

(58) Field of Classification Search
CPC . A61B 2560/0437; A61B 50/36; A61B 50/39; A61B 2217/005; A61B 2218/001;
(Continued)

(56) References Cited

U.S. PATENT DOCUMENTS 4,768,241 A 9/1988 Beney
5,971,913 A 10/1999 Newkirk et al.
(Continued)

FOREIGN PATENT DOCUMENTS

CN 202536546 U * 11/2012
CN 202554346 U 11/2012
(Continued)

OTHER PUBLICATIONS

English language abstract and machine-assisted English translation for WO 2017/103842 A1 extracted from espacenet.com database on Dec. 4, 2023, 11 pages.
(Continued)

*Primary Examiner* — Leslie R Deak
*Assistant Examiner* — Linnae E. Raymond
(74) *Attorney, Agent, or Firm* — Howard & Howard Attorneys PLLC

(57) ABSTRACT

A waste collection cart assembly for collecting waste material from a suction line during a medical procedure. The waste collection cart assembly includes a housing having a top portion defining a work surface. A waste container is
(Continued)

coupled to the housing for collecting the waste material from the suction line. A manifold receiver defining an opening is coupled to the waste container. A manifold having a specimen trap is received within the opening of the manifold receiver. A vacuum source is coupled to the waste container. The vacuum source provides a vacuum on the waste container to draw the waste material from the suction line through the manifold and into the waste container. The specimen trap collects a specimen from the waste material while being drawn into the waste container. The specimen may be transferred to a specimen container disposed on the work surface.

19 Claims, 27 Drawing Sheets

(51) Int. Cl.
*A61B 10/04* (2006.01)
*A61M 1/00* (2006.01)

(52) U.S. Cl.
CPC ............... *A61B 50/13* (2016.02); *A61M 1/60* (2021.05); *A61M 1/79* (2021.05); *A61M 1/74* (2021.05); *A61M 2205/587* (2013.01); *A61M 2209/084* (2013.01)

(58) Field of Classification Search
CPC ........ A61B 50/10–24; A61B 2050/105; A61B 2050/155; A61B 2050/185; A61B 50/13–15; A61B 50/20–24; A61M 1/60; A61M 1/64; A61M 1/71; A61M 1/77; A61M 1/80; A61M 2209/086; A61M 2205/502–505; A61M 2205/587; A47B 13/12; A47B 13/083; A47B 13/08–16; B25H 1/00–20
See application file for complete search history.

(56) References Cited

U.S. PATENT DOCUMENTS 7,615,037 B2 11/2009 Murray et al.
7,621,898 B2 11/2009 Lalomia et al.
7,715,037 B2 5/2010 Castellani et al.
8,216,199 B2 7/2012 Murray et al.
8,518,002 B2 8/2013 Murray et al.
8,740,866 B2 6/2014 Reasoner et al.
8,915,897 B2 12/2014 Murray et al.
9,579,428 B1 2/2017 Reasoner et al.
9,782,524 B2 10/2017 Reasoner et al.
9,931,451 B2 4/2018 Iske et al.
9,943,291 B2 4/2018 VanderWoude et al.
9,990,776 B2 6/2018 Jagga et al.
10,105,470 B2 10/2018 Reasoner et al.
10,471,188 B1 11/2019 Zollinger et al.
11,623,038 B2 4/2023 Hall, III et al.
2002/0166163 A1 11/2002 Shimizu
2003/0164600 A1 9/2003 Dunn et al.
2005/0171495 A1 8/2005 Austin et al.
2007/0191731 A1 8/2007 Kaye et al.
2008/0082021 A1 4/2008 Ichikawa et al.
2008/0263771 A1 10/2008 Hakamiun et al.
2009/0094734 A1 4/2009 Diebel et al.
2014/0323914 A1* 10/2014 VanderWoude .... A61M 3/0201 604/319
2014/0338529 A1 11/2014 Reasoner et al.
2015/0144514 A1* 5/2015 Brennan ................ A61B 90/50 206/363
2015/0223892 A1* 8/2015 Miller .................... A61B 50/18 345/174
2015/0342683 A1* 12/2015 Zoland ................... A61B 50/15 211/85.13
2016/0128465 A1* 5/2016 Karasina ................ A61B 50/33 108/23
2016/0367732 A1 12/2016 Reasoner et al.
2017/0234524 A1 8/2017 Schäfer et al.
2017/0258547 A1 9/2017 Karasina
2018/0185111 A1* 7/2018 Shuart .................... A61B 50/20
2018/0235583 A1 8/2018 VanderWoude et al.
2018/0333520 A1 11/2018 Mills et al.
2019/0001029 A1 1/2019 Davie et al.
2020/0168322 A1* 5/2020 Brandt ................... A61B 50/24
2021/0379322 A1* 12/2021 Maurer ................. A61M 16/16

FOREIGN PATENT DOCUMENTS

CN 204542710 U 8/2015
CN 105025948 A 11/2015
CN 204951457 U 1/2016
CN 105709290 A 6/2016
CN 206102891 U 4/2017
CN 107822808 A 3/2018
CN 207755493 U 8/2018
CN 108577969 A * 9/2018 ............ A61B 50/18
DE 102006054130 A1 7/2008
DE 102008033743 A1 4/2010
EP 1174661 A1 1/2002
WO WO-2007070570 A2 * 6/2007 ............ B01D 53/02
WO 2007103842 A2 9/2007
WO 2013090579 A1 6/2013
WO 2014066337 A2 5/2014
WO 2017023732 A1 2/2017
WO 2017070570 A1 4/2017
WO 2017103842 A1 6/2017
WO 2017112684 A1 6/2017
WO 2018170233 A1 9/2018

OTHER PUBLICATIONS

Partial International Search Report for Application No. PCT/US2020/027850 dated May 29, 2020, 2 pages.
International Search Report for Application No. PCT/US2020/027850 dated Jul. 20, 2020, 2 pages.
English language abstract and machine-assisted English translation for CN 108577969 A extracted from espacenet.com database on Oct. 13, 2021, 11 pages.
English language abstract and machine-assisted English translation for DE 10 2006 054 130 A1 extracted from espacenet.com database on Oct. 13, 2021, 11 pages.
English language abstract and machine-assisted English translation for CN 204542710 U extracted from espacenet.com database on Aug. 29, 2024, 5 pages.
English language abstract and machine-assisted English translation for CN 204951457 U extracted from espacenet.com database on Aug. 29, 2024, 8 pages.
English language abstract for CN 105025948 A extracted from espacenet.com database on Dec. 2, 2024, 2 pages.
English language abstract and machine-assisted English translation for CN 207755493 U extracted from espacenet.com database on Dec. 2, 2024, 8 pages.
English language abstract for CN 105709290 A extracted from espacenet.com database on Jul. 22, 2025, 2 pages.
English language abstract and machine-assisted English translation for CN 206102891 U extracted from espacenet.com database on Jul. 22, 2025, 6 pages.
English language abstract and machine-assisted English translation for DE 10 2008 033 743 A1 extracted from espacenet.com database on Jul. 22, 2025, 7 pages.
English language abstract and machine-assisted English translation for CN 202554346 U extracted from espacenet.com database on Mar. 3, 2025, 5 pages.
English language abstract and machine-assisted English translation for CN 107822808 A extracted from espacenet.com database on Mar. 3, 2025, 8 pages.

* cited by examiner 76
74
50
52
100
104
106
66
102
62
58
56
60
90
92

30
70
72
76
74
80
88b
88
62
88a
90
80
38
40
75b
66
150
36
34
32
34
34

WASTE COLLECTION CART FOR COLLECTING WASTE DURING A MEDICAL PROCEDURE

RELATED APPLICATIONS

This application is the National Stage entry of International Patent Application No. PCT/US2020/027850, filed Apr. 11, 2020, which claims priority to and the benefit of U.S. Provisional Application Nos. 62/833,399 and 62/849,548, filed on Apr. 12, 2019, and May 17, 2019, respectively, the entire contents of which are hereby incorporated by reference.

BACKGROUND

Waste collection carts are well known for use in health care facilities to collect waste material generated during medical procedures. Waste collection carts comprise one or more waste containers connected to a vacuum source. One or more suction lines extend from the waste containers and are positioned near the site from which the waste material is to be collected. When the vacuum source is operating, the waste material is drawn through the suction lines into the waste containers.

Waste collection carts may include a manifold having a filter element that traps large bits of solid matter. These solids may otherwise potentially clog the downstream components of the waste collection cart. In some medical procedures, such as a colonoscopy, it is desirable to collect one or more specimens from the patient during the medical procedure. To collect a specimen, a removable specimen trap is placed in series with the suction line and the manifold to be located upstream from the waste collection cart. The specimen is captured in the specimen trap during operation.

Waste collection carts are generally portable for moving throughout the health care facility. Once the waste container is full, or if an empty waste container is required prior to being full, the waste collection cart is moved to a docking station to be emptied and cleaned. The waste collection cart docks to the docking station to begin emptying. Once emptied, the waste container is cleaned by a cleaning system with detergent and rinsed.

Often, medical procedures involving specimen collection are carried out in procedure rooms having a low lighting environment where visibility of the samples and some of the accompanying equipment used during the medical procedure are not well lit. In such an environment, medical personnel may use flashlights to provide adequate lighting of the specimen.

There is a need in the art for a waste collection cart capable of overcoming one or more of the aforementioned problems.

DETAILED DESCRIPTION

Figure 1:
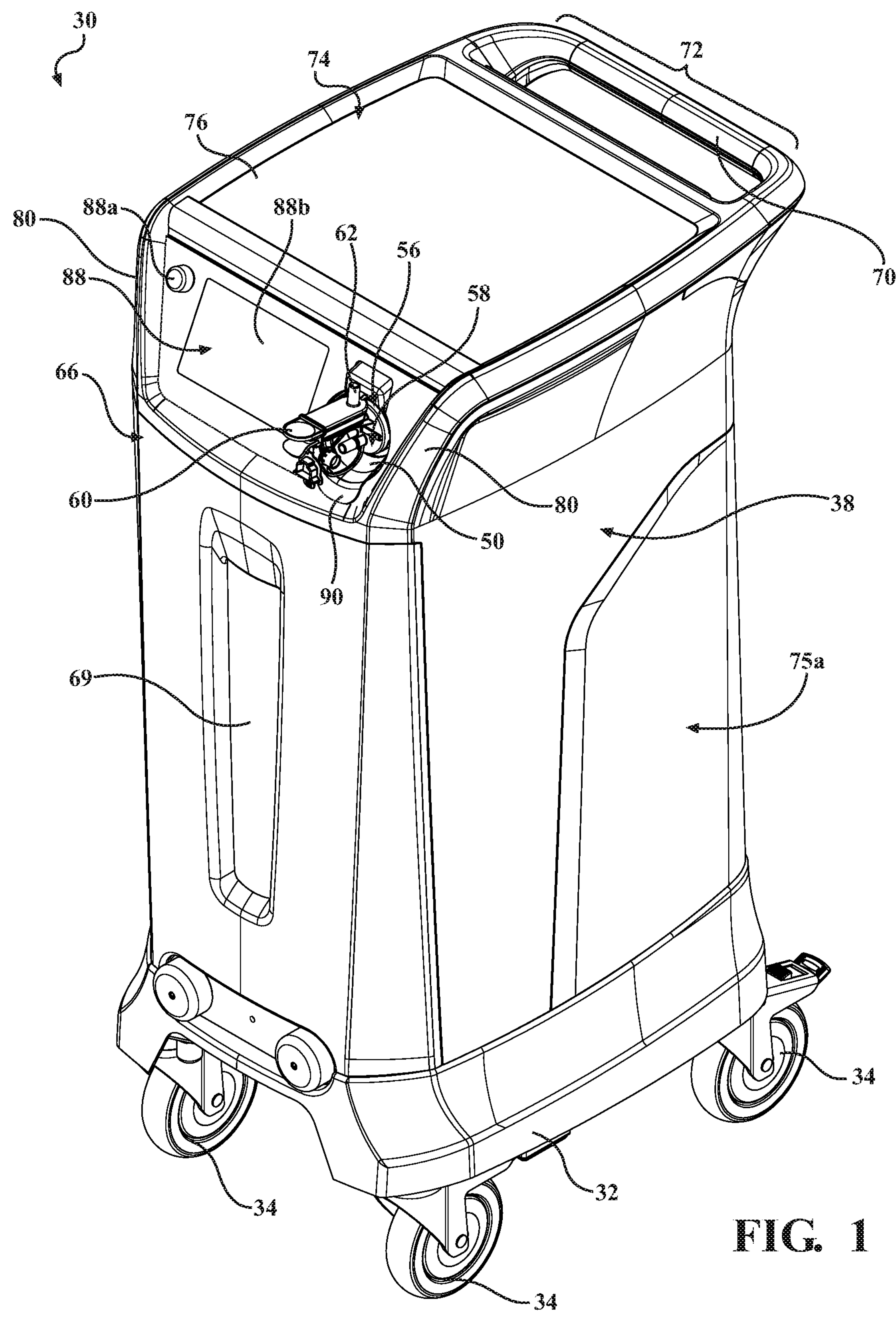
FIG. 1 is a perspective view of a waste collection cart assembly with a manifold.

With reference to the drawings, where like numerals are used to designate like structure throughout the several views, a waste collection cart assembly for collecting waste materials is shown generally at 30 in FIG. 1 for use during medical and/or surgical procedures. The waste collection cart assembly 30 collects waste material generated during medical procedures (e.g., surgical procedures) performed in a health care facility such as a hospital. The waste material may include bodily fluids, smoke, body tissues, irrigation liquids, and/or other materials that may be generated during various medical procedures. Often times, medical procedures require large amounts of saline and/or other irrigation liquids for irrigating an anatomical site. As a result, the waste collection cart assembly 30 is capable of handling large amounts of waste material. The waste collection cart assembly 30 collects the waste material for later discharge. In certain configurations, the waste collection device described herein may be a static component, i.e., not a cart.

During use, the waste collection cart assembly 30 collects the waste material and stores the waste material on-board until such time as a user is ready to off-load the waste material and dispose of the waste material. In the configurations shown, the waste collection cart assembly 30 is capable of storing waste material from a series of different medical procedures during the course of a day or across several days, without requiring off-loading of the waste material.

Figure 2:
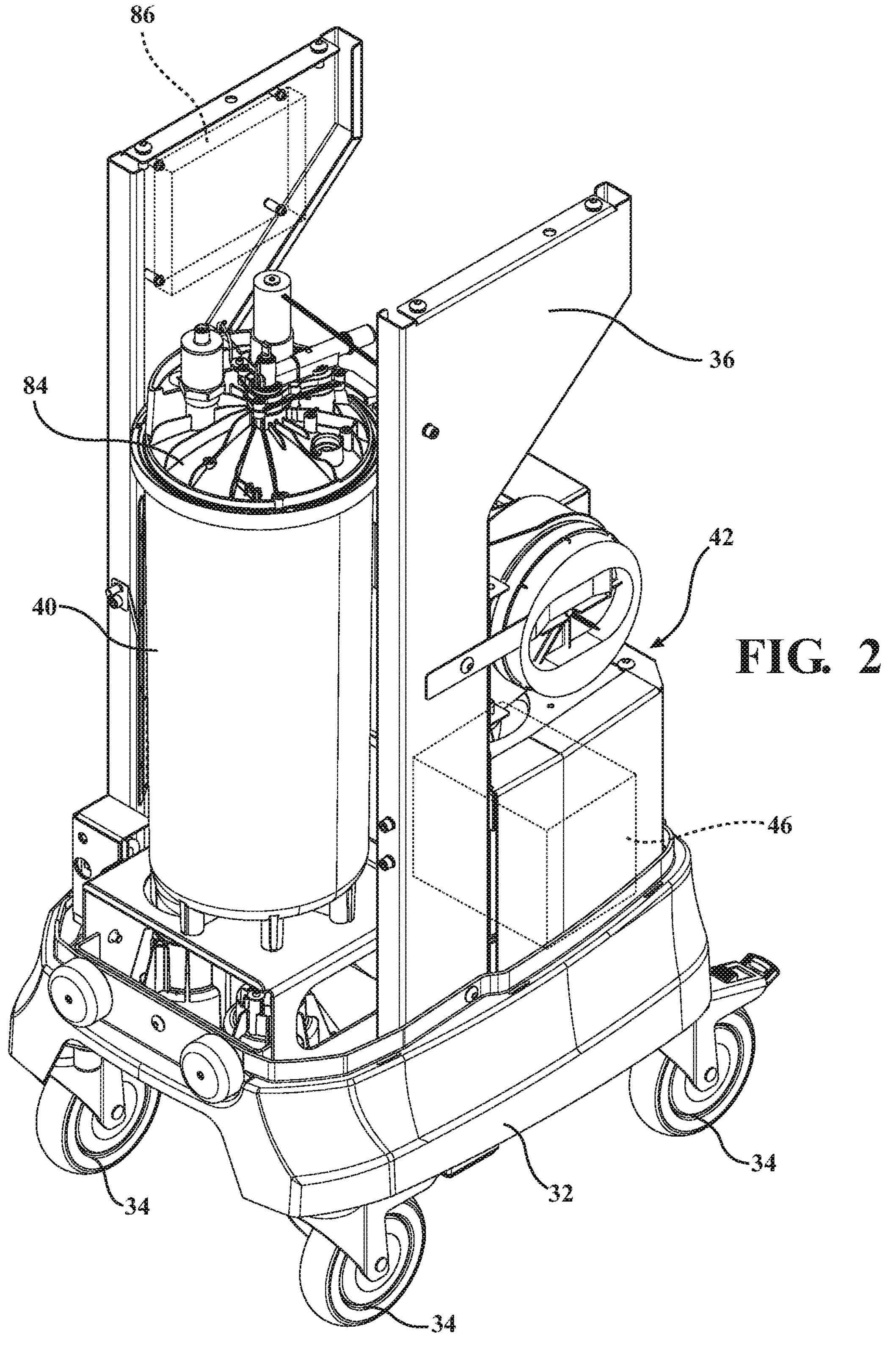
FIG. 2 is a perspective view of the waste collection cart assembly with various components removed.
Figure 3:
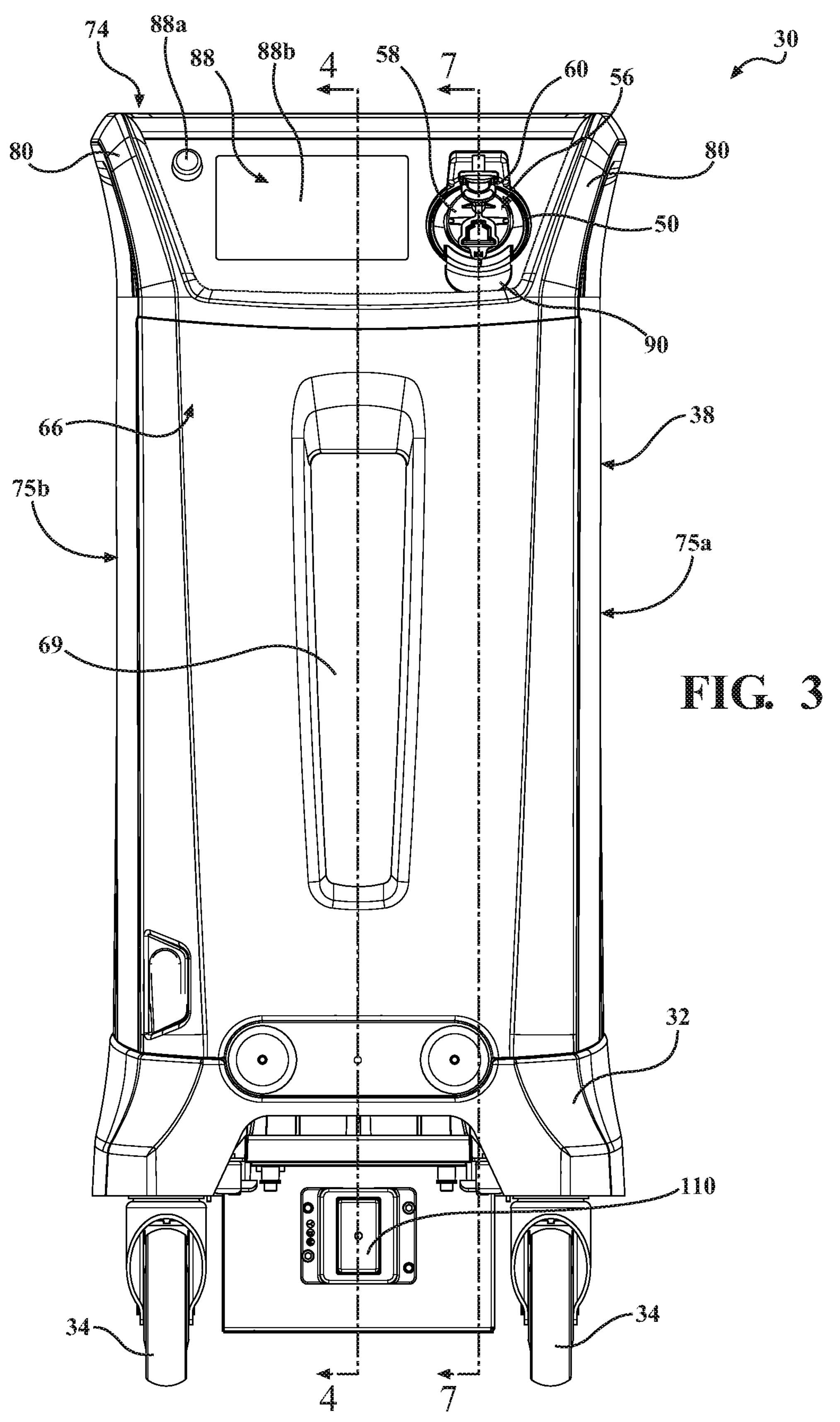
FIG. 3 is a front elevation view of the waste collection cart assembly with the manifold.

Referring to FIGS. 2 and 3, the waste collection cart assembly 30 may include a base 32 and wheels 34 for moving the waste collection cart assembly 30 along a floor surface within a medical facility. The waste collection cart assembly 30 may further include a frame or chassis 36 extending upwardly from the base 32. In one configuration, the chassis 36 comprises metal. In other configurations, the chassis 36 comprises another material configured to provide rigidity to the waste collection cart assembly 30. The waste collection cart assembly 30 includes a housing 38 (FIG. 3) defining an interior and described in further detail below. The housing 38 may comprise a polymeric material. More specifically, the housing 38 may comprise a plastic material. The housing 38 may also comprise a glass-filled nylon material to strengthen the housing 38. The waste collection cart assembly 30 further includes a waste container 40 to collect and temporarily store the waste material during use. The waste container 40 is disposed at least partially within the interior of the housing 38 and coupled to the chassis 36. It is contemplated that the waste container 40 may assume any shape that is suitable for containing the waste material. The waste container may comprise a single canister, as illustrated in the figures. The waste container 40 may be formed of glass, suitable plastic materials, or other materials.

Figure 4:
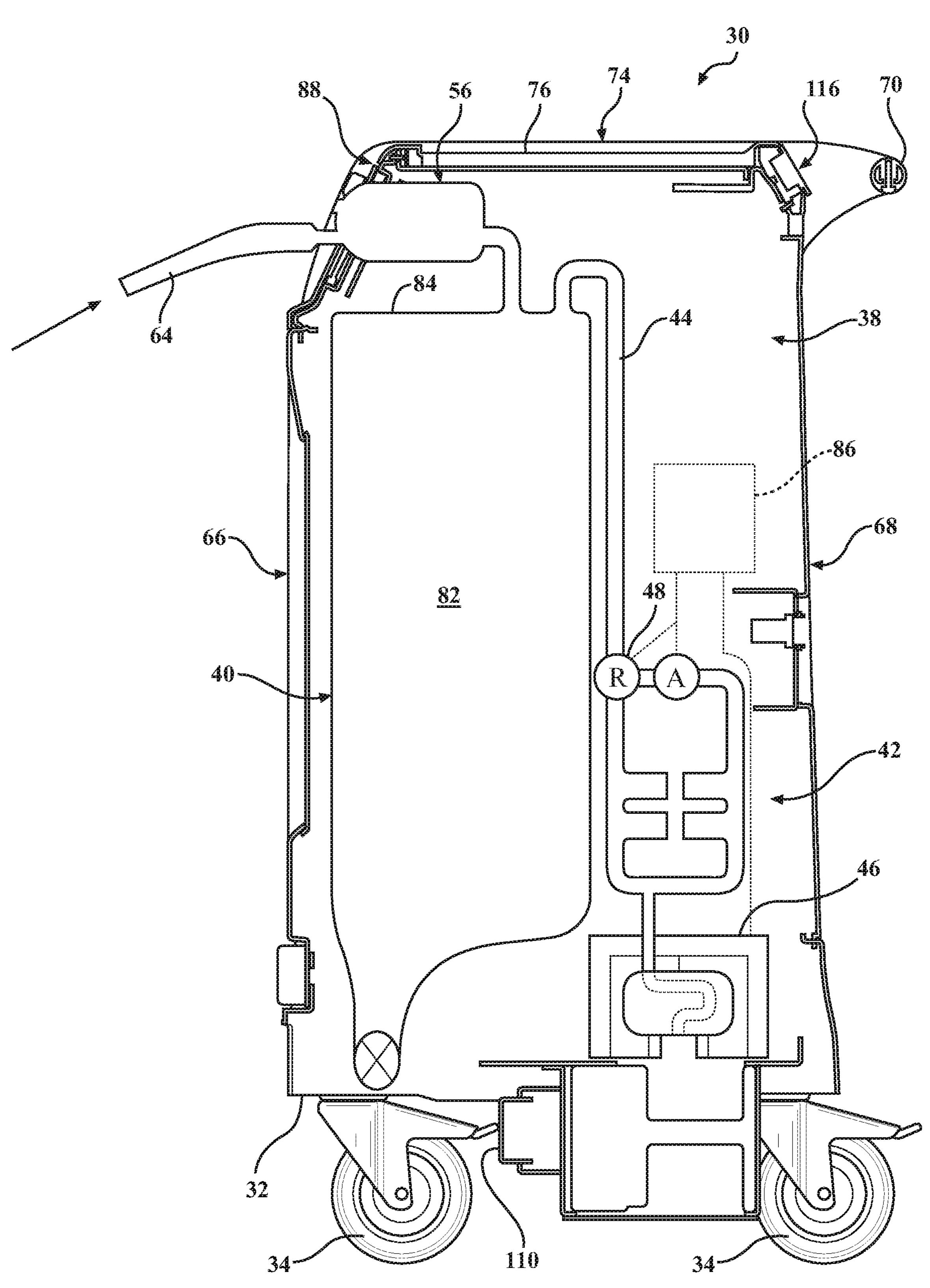
FIG. 4 is a sectional view of the waste collection cart assembly taken along line 4-4 of FIG. 3.

A vacuum source 42 may be supported on the base 32 and coupled to the chassis 36 and configured to draw suction on the waste container 40 through one or more vacuum lines 44 (shown schematically in FIG. 4). The vacuum source 42 may include a vacuum pump 46 (shown schematically in FIG. 2) such as one shown in FIG. 2. The vacuum source 42 may also include a vacuum regulator 48 (shown schematically in FIG. 4) supported on the base 32 and configured to be in fluid communication with the vacuum pump 46 and the waste container 40. The vacuum regulator 48 is configured to regulate a level of the suction drawn by the vacuum pump 46 on the waste container 40. Suitable construction and operation of several subsystems of the waste collection cart assembly 30 are disclosed in commonly owned United States Patent Publication No. 2005/0171495, published Aug. 4, 2005, International Publication No. WO 2007/070570, published Jun. 21, 2007, International Publication No. WO 2014/066337, published May 1, 2014, and International Publication No. 2017/112684, published Jun. 29, 2017, the entire contents of which are hereby incorporated by reference.

In other configurations, the vacuum source 42 may be a separate unit that can be removably coupled to the waste collection cart assembly 30 to draw suction on the waste container 40. Suitable construction and operation of such a waste collection cart assembly 30 are disclosed in commonly owned U.S. Pat. No. 10,105,470, granted Oct. 23, 2018, the entire contents of which are hereby incorporated by reference.

Figure 6A:
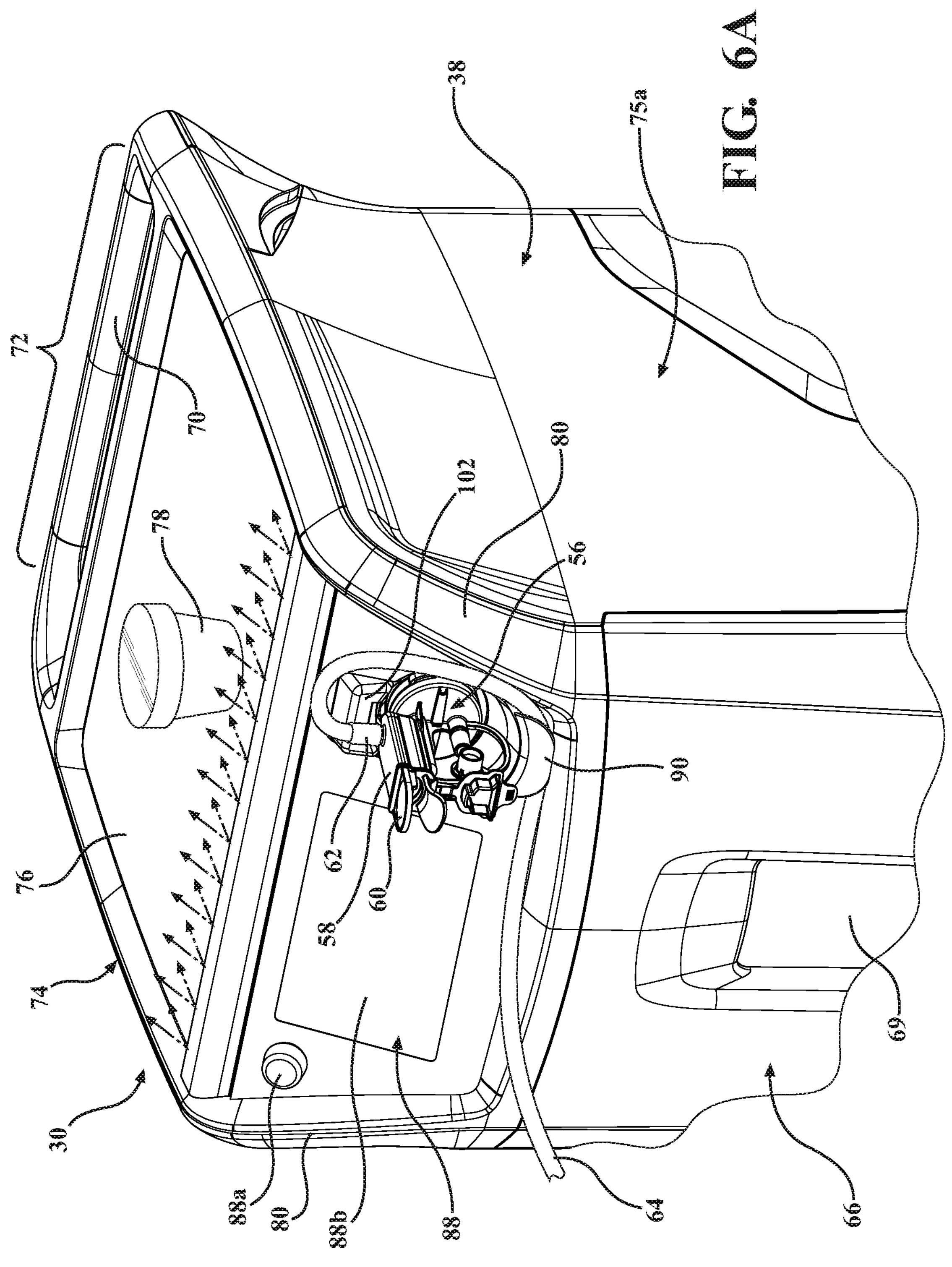
FIG. 6A is a perspective view of the waste collection cart assembly with a manifold having a specimen trap received within a manifold body and a specimen container disposed on a work surface of the top portion of the housing of the waste collection cart assembly.
Figure 6B:
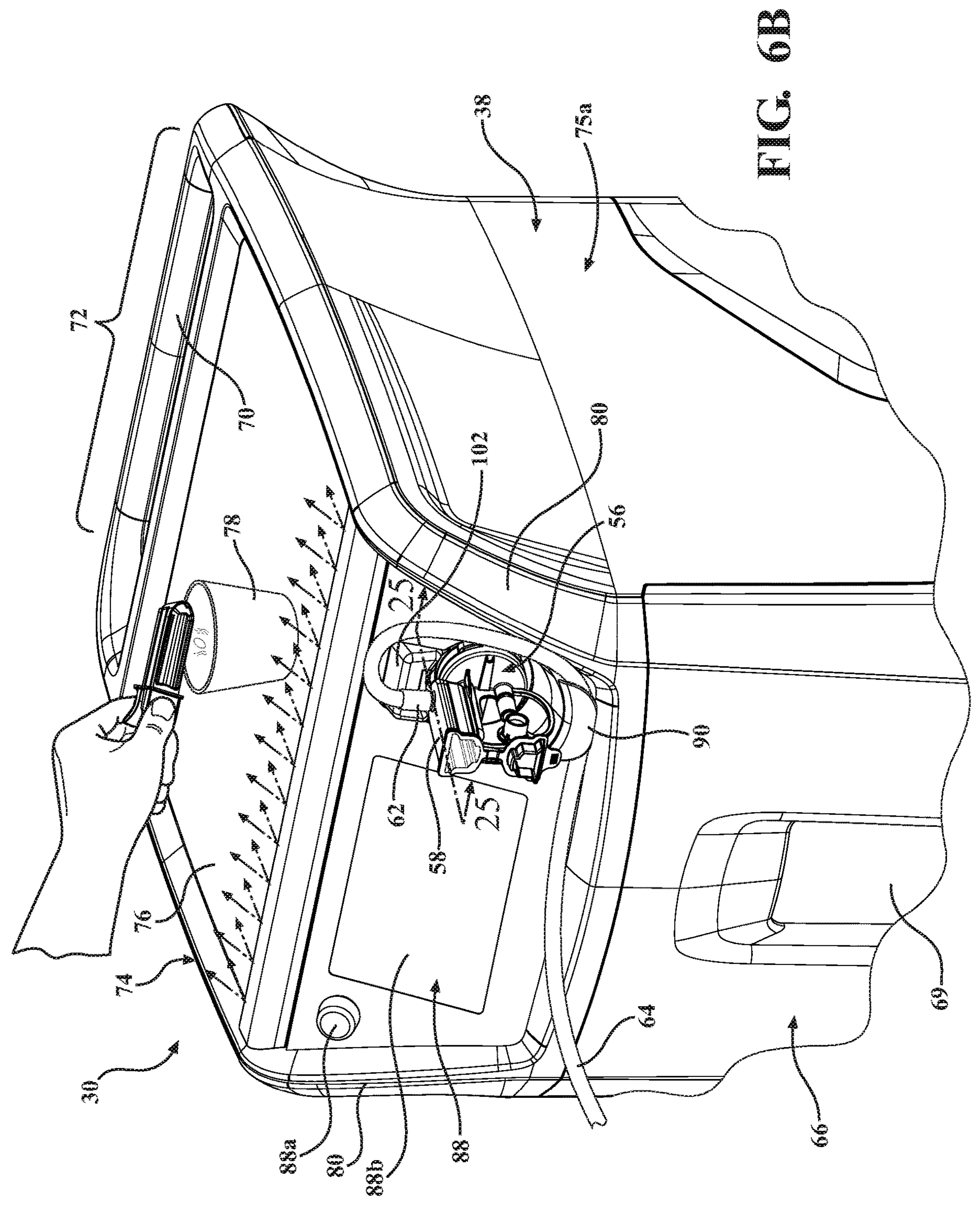
FIG. 6B is a perspective view of the waste collection cart assembly with the specimen trap removed from the manifold body and disposed above the specimen container.
Figure 7:
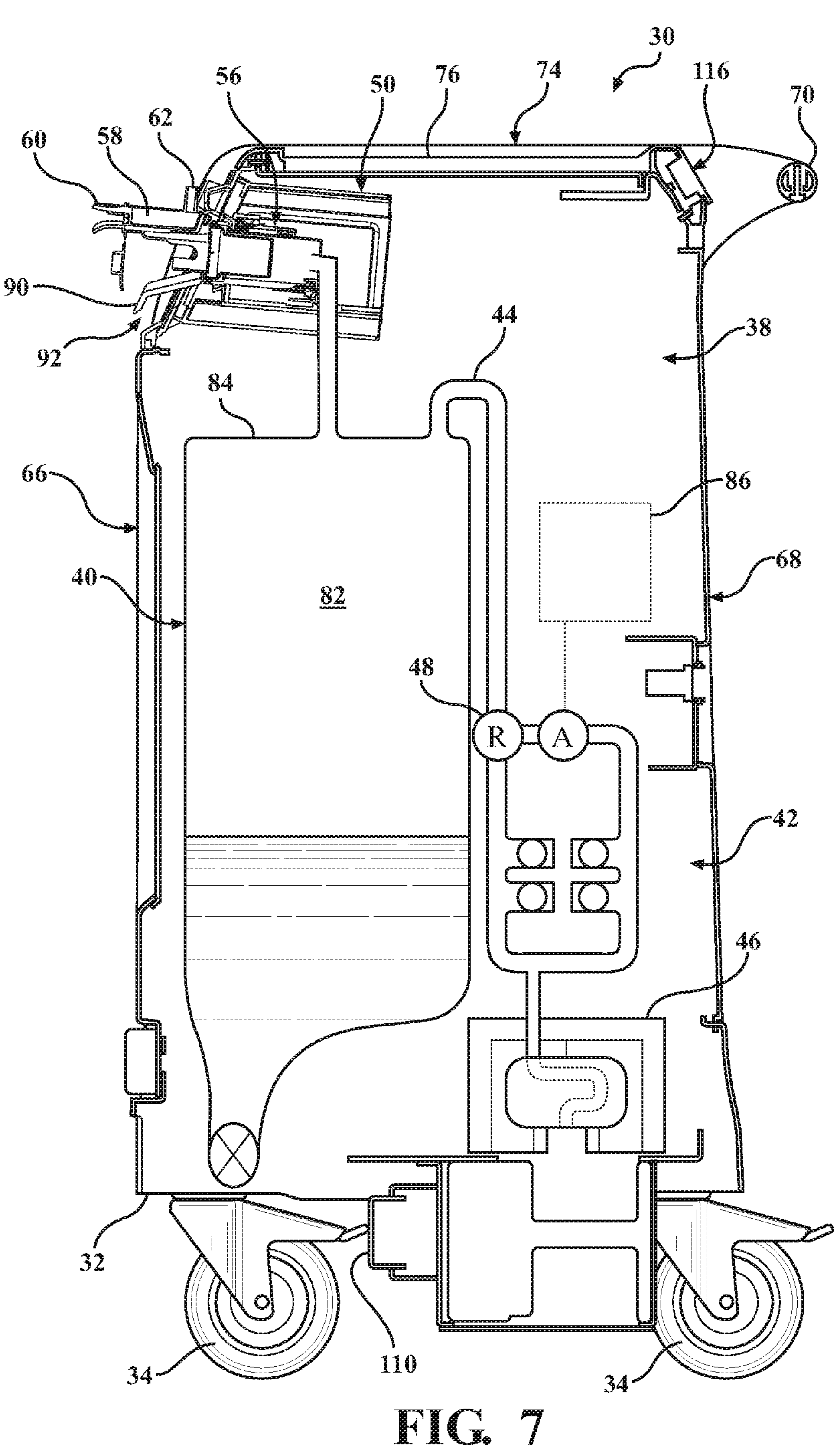
FIG. 7 is a sectional view of the waste collection cart assembly and the manifold taken along line 7-7 of FIG. 3.
Figure 16:
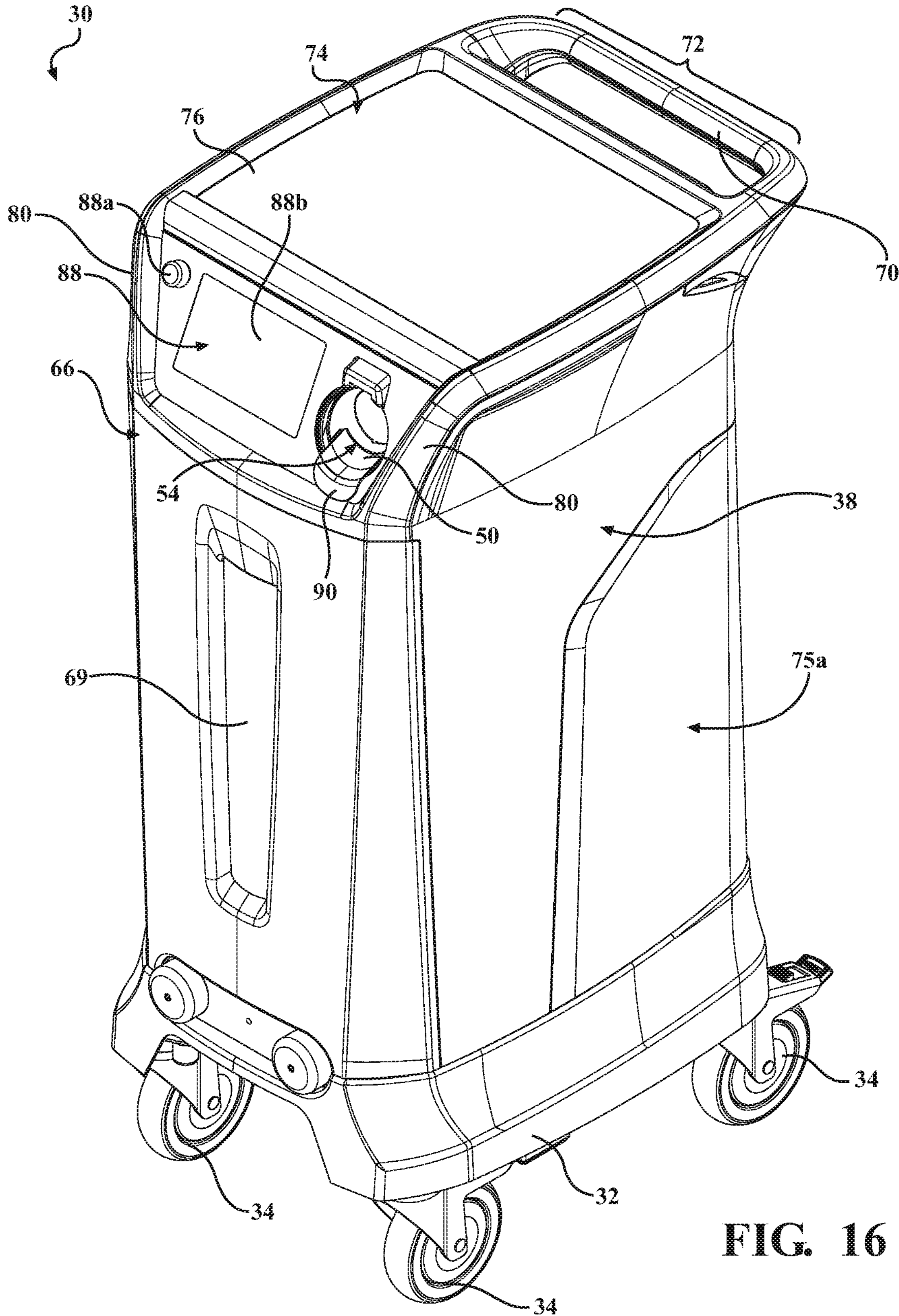
FIG. 16 is a perspective view of the waste collection cart assembly.

Referring to FIGS. 6A, 6B, and 16, the waste collection cart assembly 30 comprises a manifold receiver 50 coupled to the waste container 40 (shown in FIG. 2) and supported above the base 32. The manifold receiver 50 has an internal surface 52 defining an opening 54 (FIG. 16) to removably receive at least a portion of a manifold 56. The manifold receiver 50 is configured to facilitate fluid communication between the manifold 56 and the waste container 40 when the manifold 56 is received in the opening 54 of the manifold receiver 50.

In the illustrated configurations, the manifold 56 has a manifold body 58 and a specimen trap 60 that is removably received within the manifold body 58 for collecting a specimen (e.g., a biological sample) from a patient during the medical procedure. The specimen may be a tissue sample, a fluid sample, or any other biological sample obtained during the medical procedure. The manifold body 58 is configured to be at least partially received within the opening 54 of the manifold receiver 50. The manifold body 58 may have an inlet fitting 62 that extends above the specimen trap 60. The inlet fitting 62 is configured to be coupled to a suction line 64. During the medical procedure, the suction line 64 facilitates fluid communication from an end effector, such as an endoscope, near a procedure site, through the manifold 56 and the manifold receiver 50, and finally to the waste container 40. When the specimen trap 60 is coupled to the manifold body 58, the specimen trap 60 is configured to collect a specimen from the waste material while the waste material is being drawn into the waste container 40. One advantage of the particular configuration of the suction line 64 being coupled to the inlet fitting 62 of the manifold 56 is that the specimen trap 60 may be removed from the manifold body 58 without disconnecting the suction line 64 from the manifold 56. Suitable construction and operation of a manifold 56 is disclosed in commonly owned U.S. Pat. No. 9,943,291, granted Apr. 17, 2018, the entire contents of which are hereby incorporated by reference.

Figure 10:
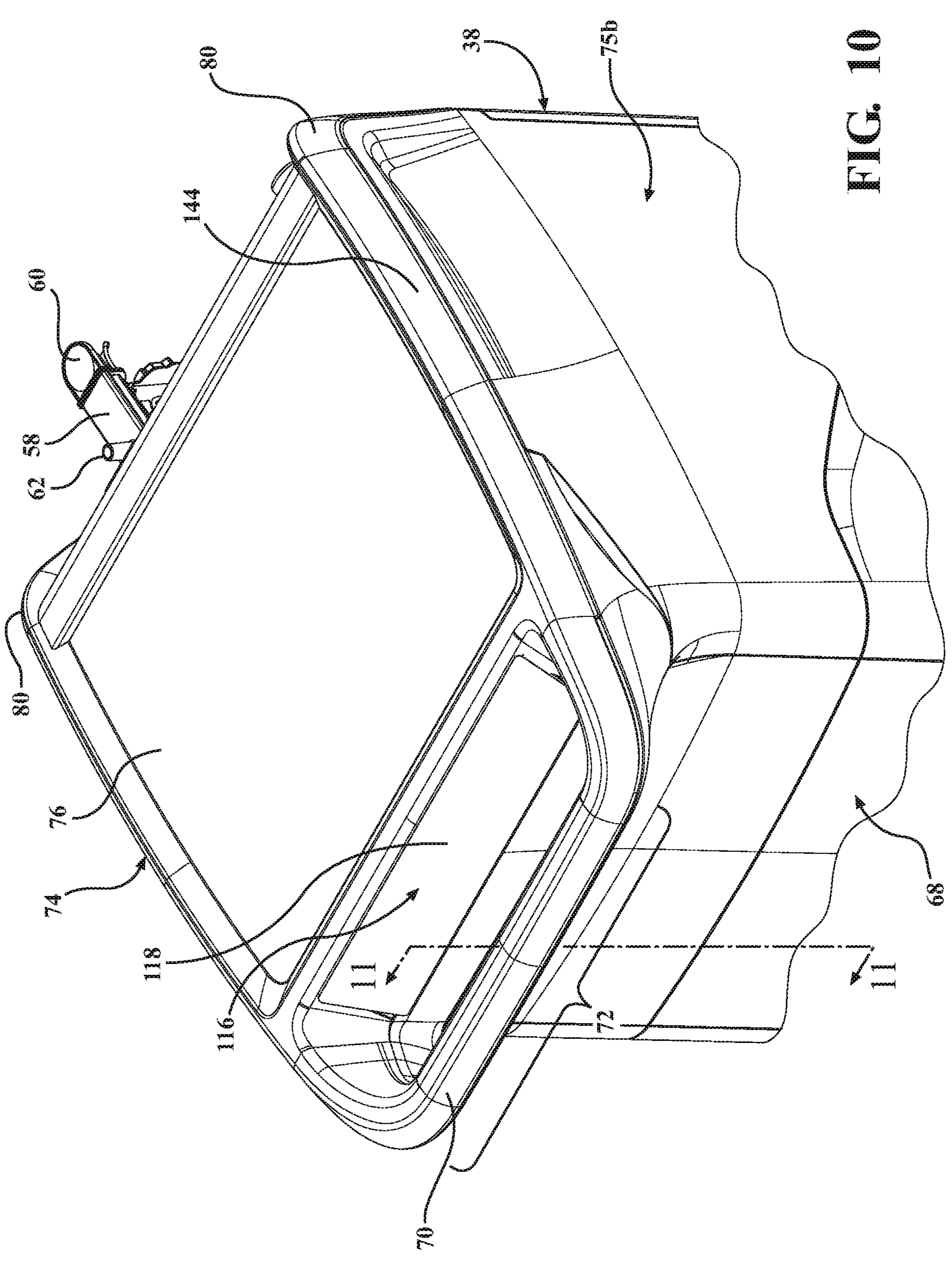
FIG. 10 is a perspective view of the top portion of the housing of the waste collection cart assembly.
Figure 14:
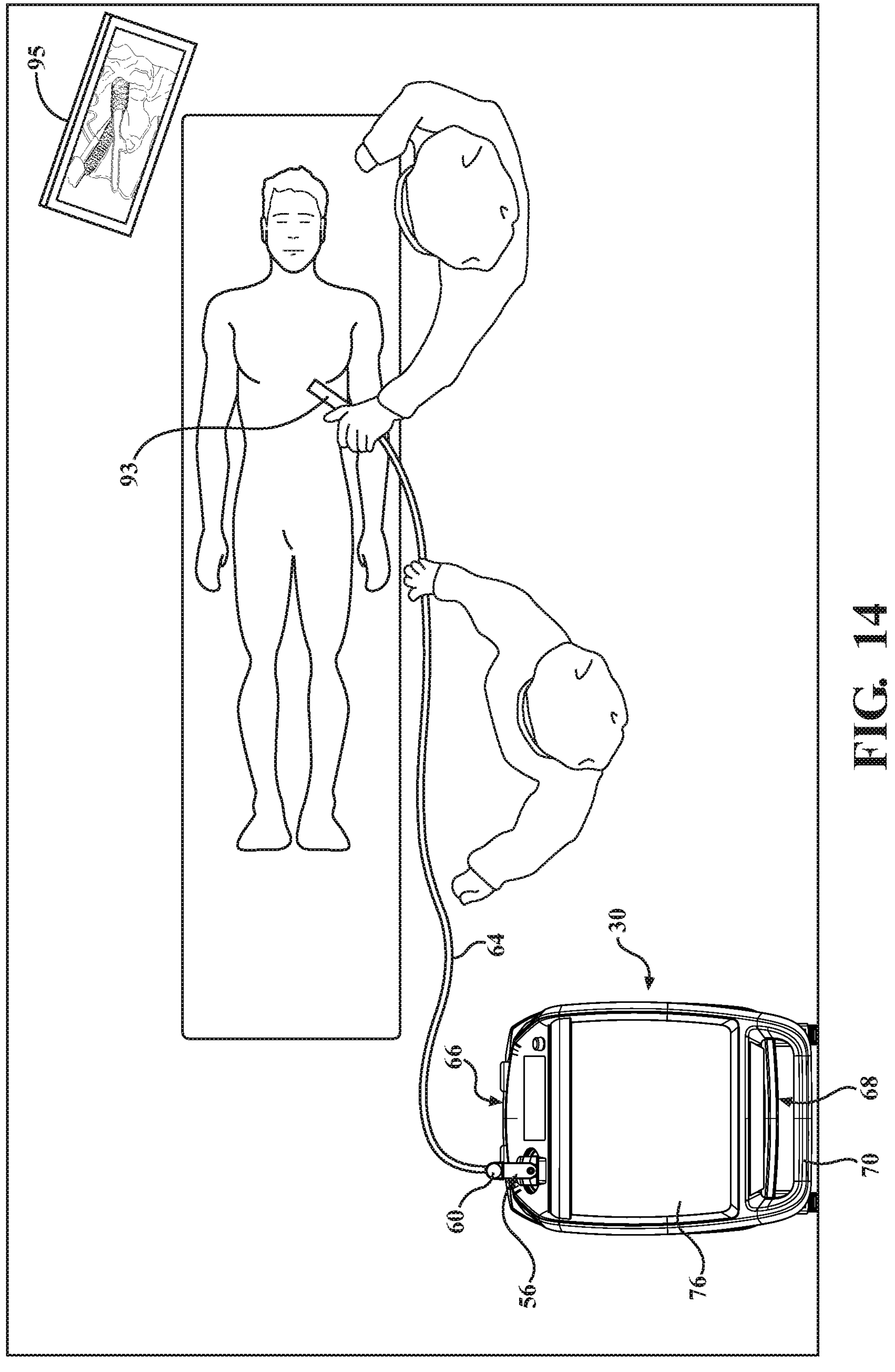
FIG. 14 is a plan view of one configuration of the waste collection cart assembly being used in a medical procedure.

Referring to FIGS. 3, 10, and 14, the housing 38 comprises a front portion 66 (see FIG. 3) adjacent the manifold receiver 50 and a back portion 68 (see FIG. 10) opposite the front portion 66. Each of the front and back portions 66, 68 of the housing 38 may comprise a single panel or multiple panels. Said differently, the front and back portions 66, 68 of the housing 38 may comprise single integral components or multiple components. The front portion 66 of the housing 38 has an exterior surface. The exterior surface of the front portion may be adapted to generally face the patient during the medical procedure (see FIG. 14). The front portion 66 of the housing 38 may have a window 69 to permit a user to view the waste container 40. When the waste container 40 comprises a transparent material such as glass, the user can see the waste material in the waste container 40 through the window 69. When the waste container 40 comprises a transparent or translucent material, the user can see a level of waste material in the waste container 40. In the configuration illustrated in FIG. 3, the window 69 is shown generally in the center (side to side) of the front portion 66 of the housing 38. However, it is contemplated that the window 69 may be disposed off-center such that the window is disposed to the left or right of the position of the window 69 as viewed in FIG. 3.

Figure 17:
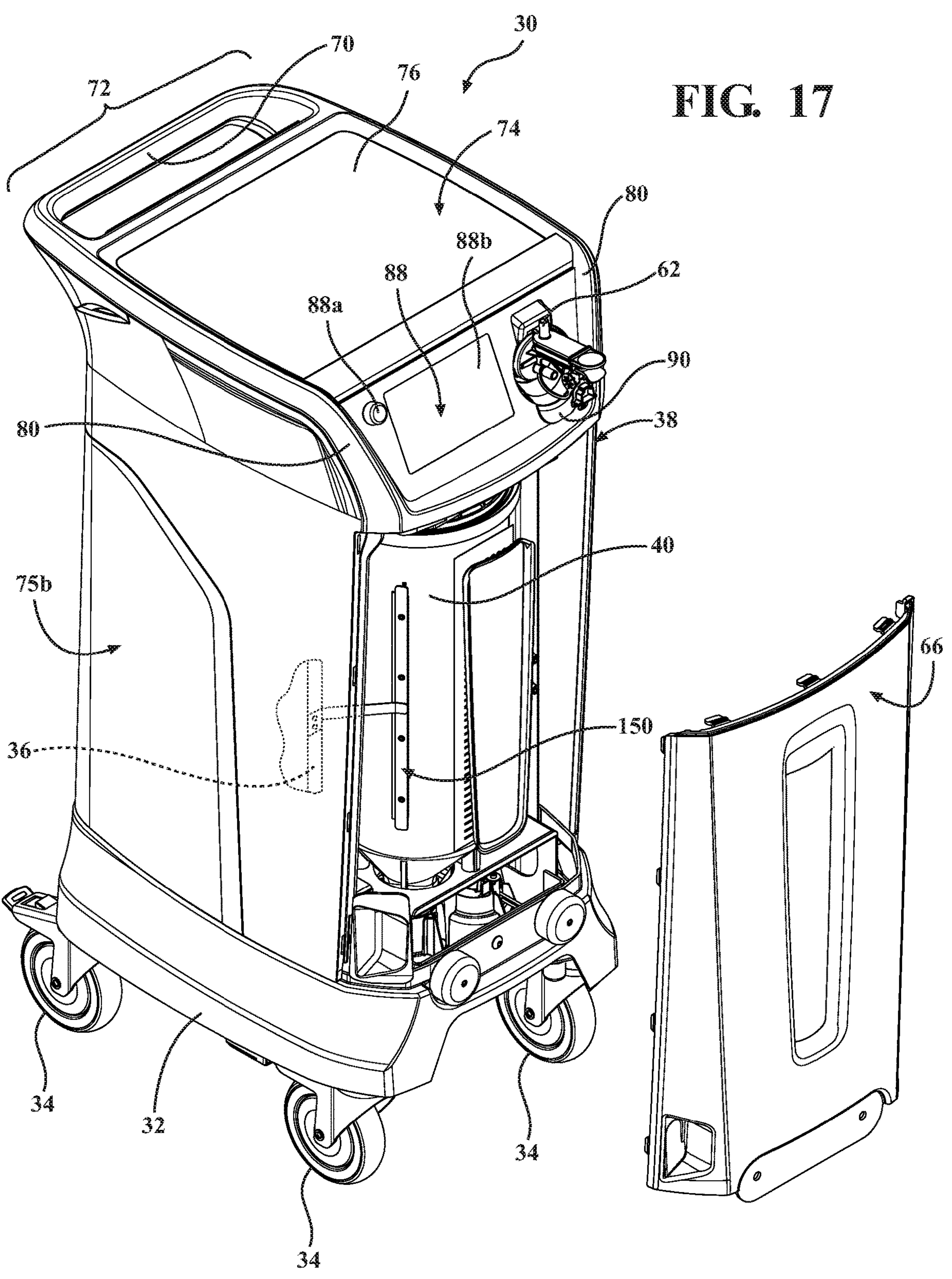
FIG. 17 is a partial perspective view of the waste collection cart assembly with a front portion of the housing exploded from the rest of the housing.
Figure 18:
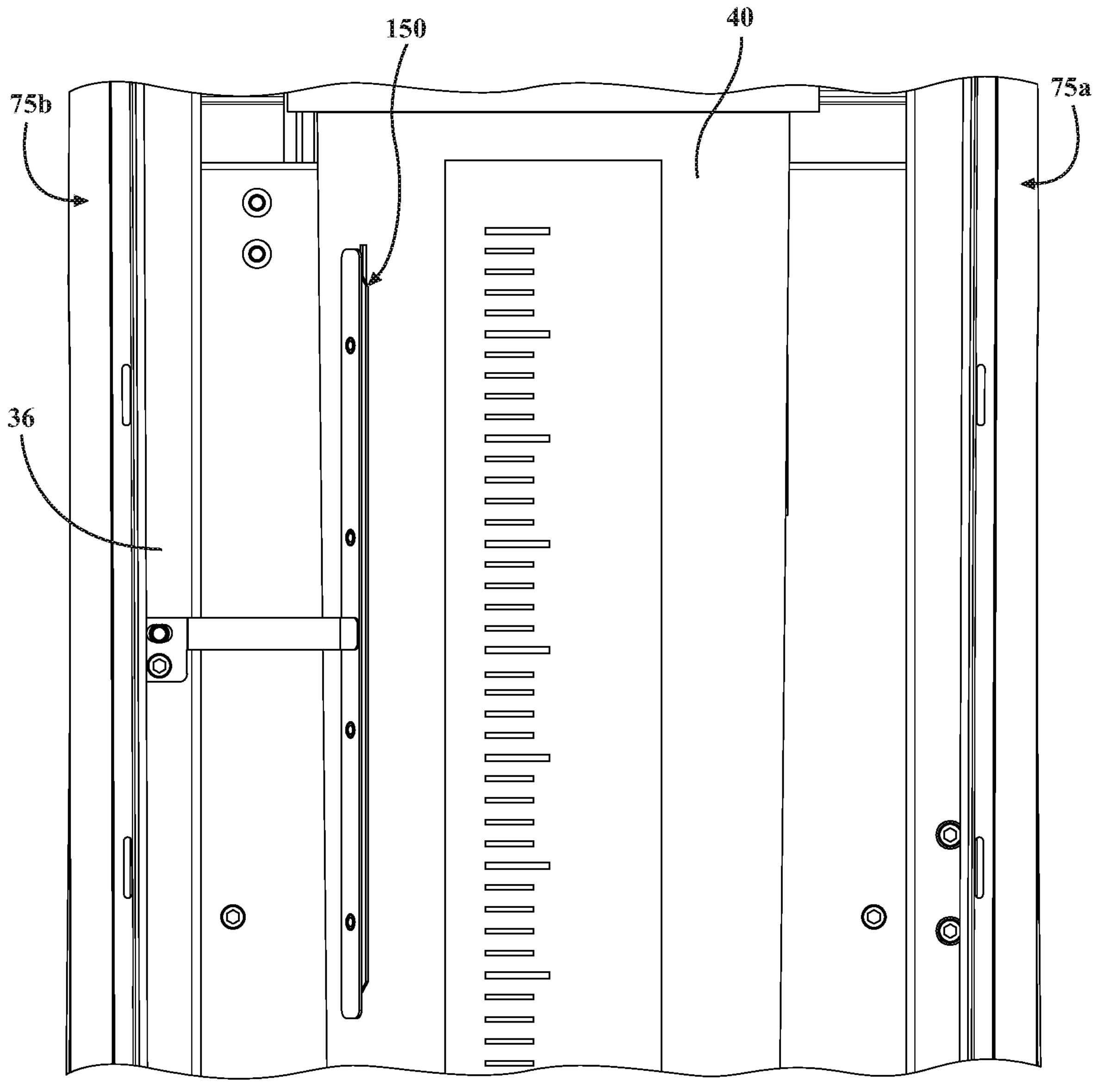
FIG. 18 is an elevation view of a waste container of the waste collection cart assembly and a light source array of the waste collection cart assembly.
Figure 19:
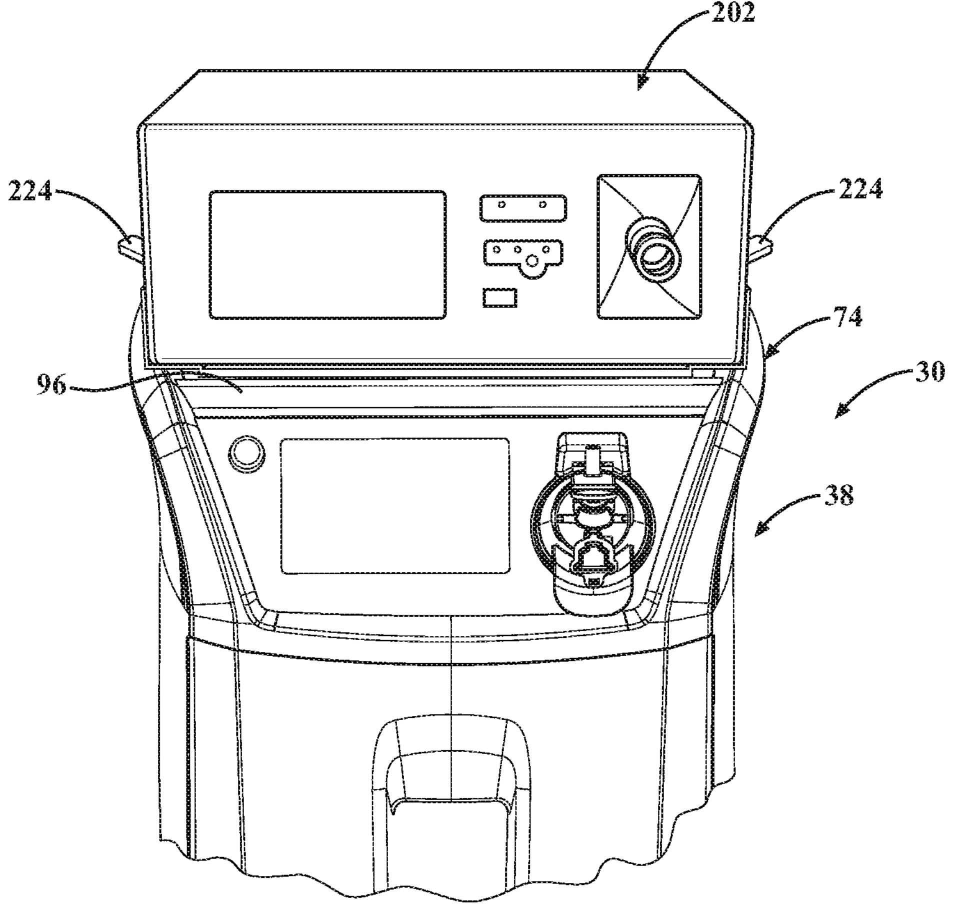
FIG. 19 is a partial perspective view of a medical module secured to the waste collection cart assembly.

Referring to FIGS. 17 and 18, the waste collection cart assembly 30 may be configured to be illuminated internally to assist the user in observing the level of waste material in the waste container 40. In one configuration, the waste collection cart assembly 30 includes a light source array 150 coupled to the chassis 36 and configured to project light onto the waste container 40. In some configurations, the light source array 150 may be coupled to the waste container 40 to project light into the waste container 40 when the waste container 40 comprises a translucent or transparent material. In one configuration the light projected is a low-intensity light. The light source array 150 may comprise a plurality of light sources to illuminate the waste container 40. However, it is also contemplated that the light source array 150 could instead comprise a single light source for illuminating the waste container 40. The light source array 150 may comprise one or more light sources selected from a light emitting diode, a bulb, a lamp, or another like device configured to emit visible light. In the configuration illustrated, the light source array 150 is configured to project light away from the front portion 66 of the housing 38. It is contemplated that the light source array 150 may be positioned elsewhere relative to the waste container 40 such that the light source array 150 projects light onto or into the waste container 40 in a different direction. Providing the light source array 150 mitigates the need for an external lighting source such as a flashlight.

As mentioned above, the manifold 56 is received by the manifold receiver 50. Thus, it is advantageous to arrange the waste collection cart assembly 30 such that the front portion 66 of the housing 38 faces the patient during the medical procedure (shown in FIG. 14) to provide a more direct route for the suction line 64 from the patient to the manifold 56 and to provide greater access of the manifold 56 to the user. In other words, the back portion 68 of the housing 38 may face the outer walls of the procedure room and the front portion 66 of the housing 38 may face towards the interior of the procedure room. In configurations of the waste collection cart assembly 30 including the light source array 150 for illuminating the waste container 40, the light source array may be configured to project light in a direction that mitigates light being projected toward the front portion 66 of the housing 38 and thus, mitigates light being projected toward the patient/procedure site in the procedure room during the medical procedure. It is contemplated that the external surface of the front portion 66 of the housing 38 need not face the patient during the medical procedure.

Referring to FIG. 10, the back portion 68 of the housing 38 has an external surface facing away from the front portion 66 of the housing 38. The back portion 68 of the housing 38 may comprise a handle 70 to facilitate movement of the waste collection cart assembly 30 between use areas, and between the use areas and a docking station (described in greater detail further below). Thus, the user may move the waste collection cart assembly 30 around the health care facility to collect waste material generated during medical procedures performed in different locations throughout the health care facility. In the configuration illustrated in FIG. 10, the handle 70 is integral with the back portion 68 of the housing 38. However, it is contemplated that the handle 70 may instead be a separate component coupled to the back portion 68 of the housing 38.

The handle 70 projects away from the external surface of the back portion 68 of the housing 38 and has a grasping section 72 spaced from the back portion 68 of the housing 38. The grasping section 72 of the handle 70 and the external surface of the back portion 68 of the housing 38 collectively define a void therebetween to accommodate placement of the user's hand.

Referring to FIGS. 6A and 6B, the housing 38 includes a top portion 74 disposed between the front and back portions 66, 68 of the housing 38. The housing 38 further includes side portions 75*a* (See FIG. 6A), 75*b* (see FIG. 10) disposed between the front and back portions 66, 68 of the housing 38 and below the top portion 74 of the housing 38. The top portion 74 of the housing 38 has a work surface 76 for supporting a variety medical tools and equipment. In one configuration, the work surface 76 is configured to support a specimen container 78 (e.g., a formalin jar) for collecting a specimen obtained in the specimen trap 60. The specimen container 78 may provide a more suitable enclosure for transporting the specimen than the specimen trap 60. The work surface 76 is disposed above the manifold receiver 50 for ease of accessibility during the transfer of the specimen from the specimen trap 60 to the specimen container 78. As will be described in greater detail further below, the work surface 76 may be generally planar and parallel to the floor surface. Said differently, the work surface 76 may be generally planar and configured to be level with respect to gravity when resting. Further, the work surface 76 may be set into the top portion 74 of the housing 38. In one configuration, the work surface 76 has a surface area of at least 100 $in.^2$ In another configuration, the work surface 76 has a surface area of at least 150 $in.^2$ It is contemplated that the surface area may be less than 100 $in.^2$ The waste collection cart assembly 30 may be shorter and may have a smaller footprint than conventional waste collection cart assemblies. In many configurations, a maximum height of the waste collection cart assembly 30 is selected to keep the work surface 76 at a comfortable height above the floor surface for the user to interact with tools and equipment disposed on the work surface 76. More specifically, the waste collection cart assembly 30 has a maximum height defined between a bottom of the wheels 34 and a top of the top portion 74 of the housing 38. In one configuration, the maximum height is not more than 45 in. In another configuration, the maximum height is not more than 42.5 in. In still another configuration, the maximum height is not more than 40 in. In the above configurations, the work surface 76 may be set into the top portion 74 of the housing 38 between 0.25 in. and 3.0 in. such that a height between the work surface and the wheels 34 is 0.25 in to 3.0 less than the maximum height of the waste collection cart assembly 30. It is contemplated that the work surface 76 may be set into the top portion 74 of the housing 38 more than 3.0 in. It is also contemplated that the work surface 76 may be set into the top portion 74 of the housing 38 less than 0.25 in.

The smaller footprint may permit the waste collection cart assembly 30 to fit into smaller rooms in the healthcare facility. The footprint of the waste collection cart assembly 30 is defined by a width and a depth of the waste collection cart assembly 30. The waste collection cart assembly 30 has a maximum depth defined between the front and back portions 66, 68 of the housing 38. In one configuration, the maximum depth is not more than 24 in. In another configuration, the maximum depth is not more than 23 in. In still another configuration, the maximum depth is not more than 22 in. The waste collection cart assembly has a maximum width defined between the side portions 75*a*, 75*b* of the housing 38. In one configuration, the maximum width is not more than 19 in. In another configuration, the maximum width is not more than 18 in. In still another configuration, the maximum width is not more than 17 in.

The housing 38 may include one or more side handles 80 formed by one or more of the front, back, and top portions 66, 68, 74 of the housing 38. The side handles 80 may be used to facilitate movement of the waste collection cart assembly 30 across the floor surface. The side handles 80 may be suitable for making small adjustments to the position of the waste collection cart assembly 30 across the floor surface, such as pulling the waste collection cart assembly 30 away from the wall of the procedure room when the back portion 68 of the housing 38 is adjacent the wall, or for moving the waste collection cart assembly 30 laterally.

Referring to FIG. 4, a schematic representation of waste material being collected by the waste collection cart assembly 30 is shown. The waste container 40 defines a waste chamber 82 for holding the waste material. The waste container 40 includes a cap 84 to close the waste chamber. A vacuum is pulled on the waste container 40 from the vacuum source 42 to draw the waste material into the waste container 40 through the suction line 64 and the manifold 56 from a procedure site.

The waste collection cart assembly 30 comprises a cart controller 86 (shown schematically in FIGS. 2 and 4). The cart controller 86 may comprise a plurality of sub-controllers, each including one or more microprocessors, processors, systems on a chip, etc. to operate certain features of the waste collection cart assembly 30. The sub-controllers may communicate with the cart controller 86 along a communications bus or by other conventional methods. An on-board control panel 88, described in further detail below is configured to generate signals to and receive signals from the cart controller 86 to permit a user to selectively operate the vacuum source 42 and other systems of the waste collection cart assembly 30.

In one configuration, the cart controller 86 is configured to generate signals to the vacuum regulator 48 to operate the vacuum regulator 48 to adjust the vacuum level in the waste container 40. In another configuration, the cart controller 86 is configured to generate signals directly to the vacuum pump 46 and operate the vacuum pump 46 to adjust the vacuum level in the waste container 40.

In the configuration illustrated in FIGS. 6A-6B, the control panel 88 is coupled to the front portion 66 of the housing 38 adjacent the manifold receiver 50. The proximity of control panel 88 to the manifold receiver 50 provides advantageous accessibility to the user for both the operation of the vacuum source 42 via the control panel 88 and the specimen trap 60. The control panel 88 may comprise one or more knobs 88*a*, dials, touch screen inputs 88*b*, or the like, in communication with the cart controller 86, to allow the user to establish the desired vacuum levels in the waste container 40. The control panel 88 may also be configured to indicate to the user data relating to suction level on the waste container 40. Suitable operation of a waste collection cart assembly 30 to control vacuum levels in a waste container 40 are disclosed in commonly owned U.S. Pat. No. 7,621,898, granted Nov. 24, 2009, the entire contents of which are hereby incorporated by reference.

Figure 8:
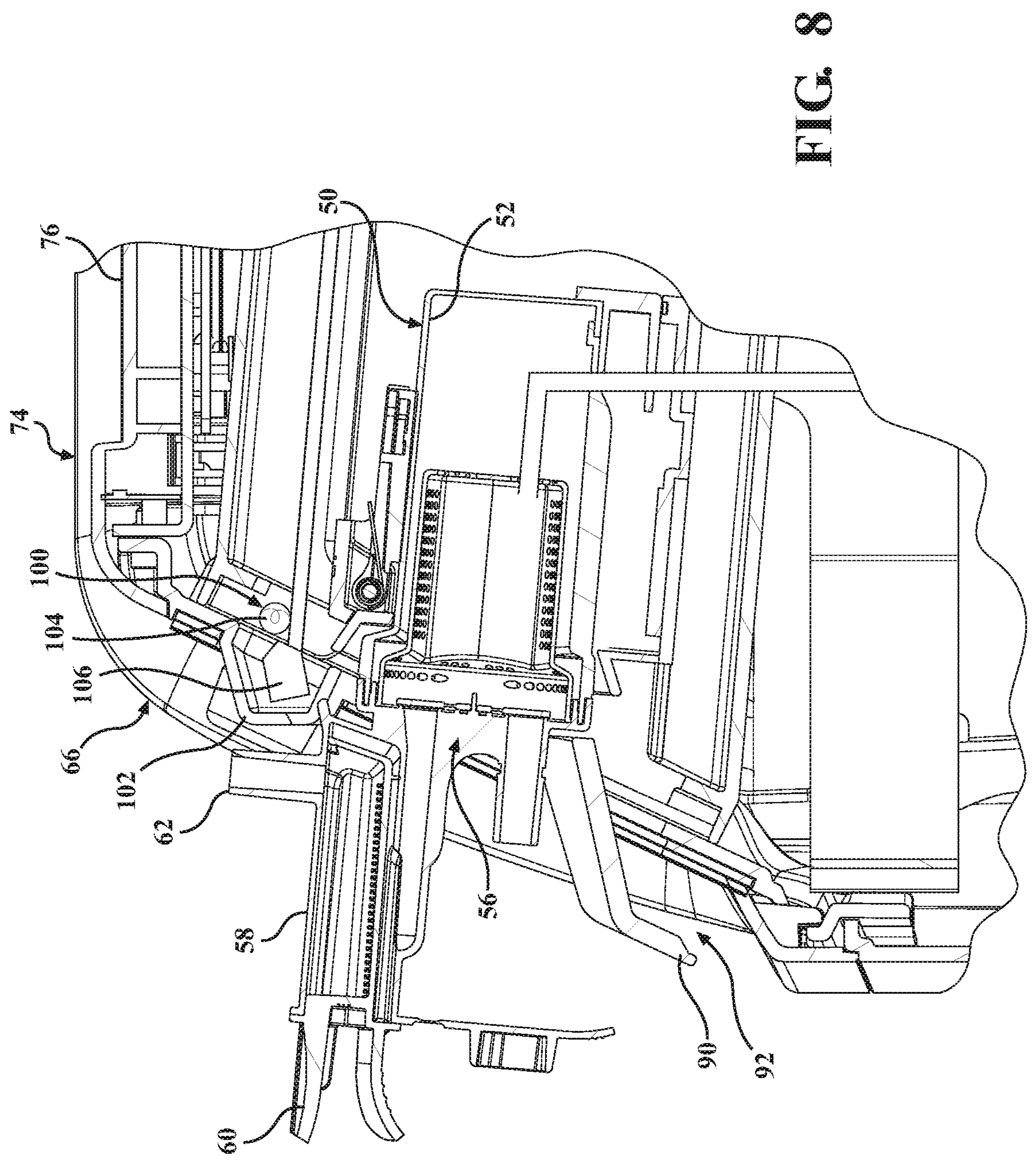
FIG. 8 is another sectional view of the waste collection cart assembly and the manifold taken along line 7-7 of FIG. 3 illustrating a trap light assembly.

Referring to FIGS. 6A, 6B, and 8, one of the housing 38 and the manifold receiver 50 comprises a line management member 90 projecting outwardly from the front portion 66 of the housing 38 adjacent the manifold receiver 50. The line management member 90 and the external surface of the front portion 66 of the housing 38 collectively defining a void 92 to receive the suction line 64. The suction line 64 may be directed by the line management member 90 to the inlet fitting 62 of the manifold body 58. In this manner, the suction line 64 may be directed away from one or both of the specimen trap 60 and the control panel 88. By directing the suction line 64 away from the control panel 88, the suction line's 64 interference with the user's view/access of the control panel 88 is mitigated. By directing the suction line 64 away from the specimen trap 60, the specimen trap 60 may be removed from the manifold body 58 without catching on or otherwise contacting the suction line 64. The line management member 90 may be integrally formed with the housing 38. While FIGS. 6A, 6B, and 8 show the line management member 90 used in connection with the specimen trap 60, it is contemplated that the line management member 90 may be used in configurations of the waste collection cart assembly 30 where the manifold does not include a specimen trap 60. While the line management member 90 is shown extending beneath the opening 54 of the manifold receiver 50, it is contemplated that the line management member 90 may be disposed at different positions relative to the opening 54 of the receiver 50 e.g., above, alongside, etc.

In the configuration illustrated in FIGS. 5A-6B, a light source assembly 94 is coupled to the housing 38 adjacent the front portion 66 of the housing 38 and configured to illuminate the work surface 76 of the top portion 74 of the housing 38 to provide enhanced visibility of the work surface 76. In one configuration, the light projected from the light source is a low-intensity light. The light source assembly 94 may project light away from the opening 54 of the manifold receiver 50 toward the back portion 68 of the housing 38. In other words, referring to FIG. 14, the light source assembly 94 may be configured to project light in a direction that mitigates light being projected toward the front portion 66 of the housing 38 and thus, mitigates light being projected toward the patient/procedure site in the procedure room during the medical procedure.

During a medical procedure in which a specimen is collected by the specimen trap 60, such as a gastrointestinal endoscopic procedure (GI procedure), the specimen may be transferred to the specimen container 78 for further analysis or transferred to the specimen container 78 for another purpose. It is contemplated that medical procedures other than GI procedures may be conducted in which a specimen may be collected by the specimen trap 60. Medical procedures involving the collection of specimens are often conducted in procedure rooms where the environment surrounding the patient (e.g., equipment in the room spaced from the procedure site) is dimly lit.

In one configuration illustrated in FIG. 14, and in many GI procedures, it is important that the procedure room remain dark or dimly lit so that an endoscope 93 used during the procedure can effectively capture images of the procedure site for later analysis and display them on a monitor 95 in the procedure room without light in the procedure room producing a glare on the monitor 95. Ambient light and artificial light projected on the monitor 95 may impair the user's ability to view the images captured by the endoscope 93. With the arrangement of the exterior surface of the front portion 66 of the housing 38 generally facing the patient/procedure site and the light source assembly 94 projecting light onto the work surface 76 away from the front portion 66 of the housing 38, the illuminated work surface 76 may be utilized without projecting light toward the monitor 95 and without compromising the quality of images viewed on the monitor 95.

In dimly lit environments, the transfer of the specimen from the specimen trap 60 to the specimen container 78 can be difficult and may prompt a user to remove the specimen trap 60, which is adjacent the procedure site, and walk toward an area of the procedure room or another room that is better illuminated. Illuminating the work surface 76 of the top portion 74 of the housing 38 provides a light built into the waste collection cart assembly 30 for users to transfer the specimen collected in the specimen trap 60 to the specimen container 78 while the specimen container 78 is disposed on the work surface 76. Further, removal of the specimen trap 60 with the specimen and transfer of the specimen to the specimen container 78 may be accomplished while the user is standing next to the waste collection cart assembly 30. One advantage of such a configuration is a more efficient workflow, as the user may not be required to leave their station adjacent the waste collection cart assembly 30 to transfer the specimen elsewhere. Another advantage of permitting the user to stand in place while removing the specimen trap 60 from the manifold body 58 and transferring the specimen to the specimen container 78 is reducing the opportunity for a user to drop a sample while walking to an illuminated environment.

Figure 5A:
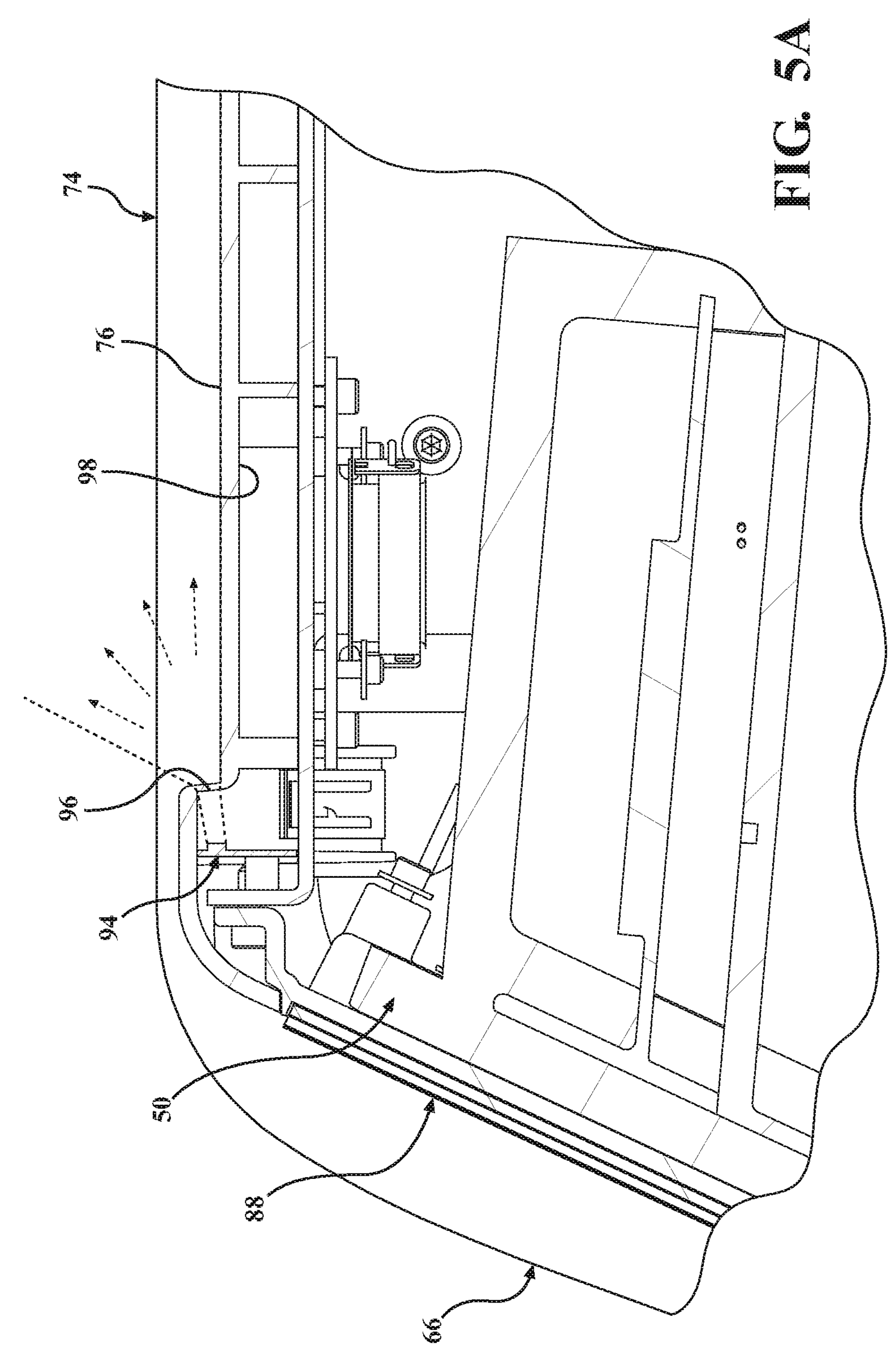
FIG. 5A is another sectional view of the waste collection cart assembly taken along line 4-4 of FIG. 3 illustrating a top portion of a housing of the waste collection cart assembly.
Figure 5B:
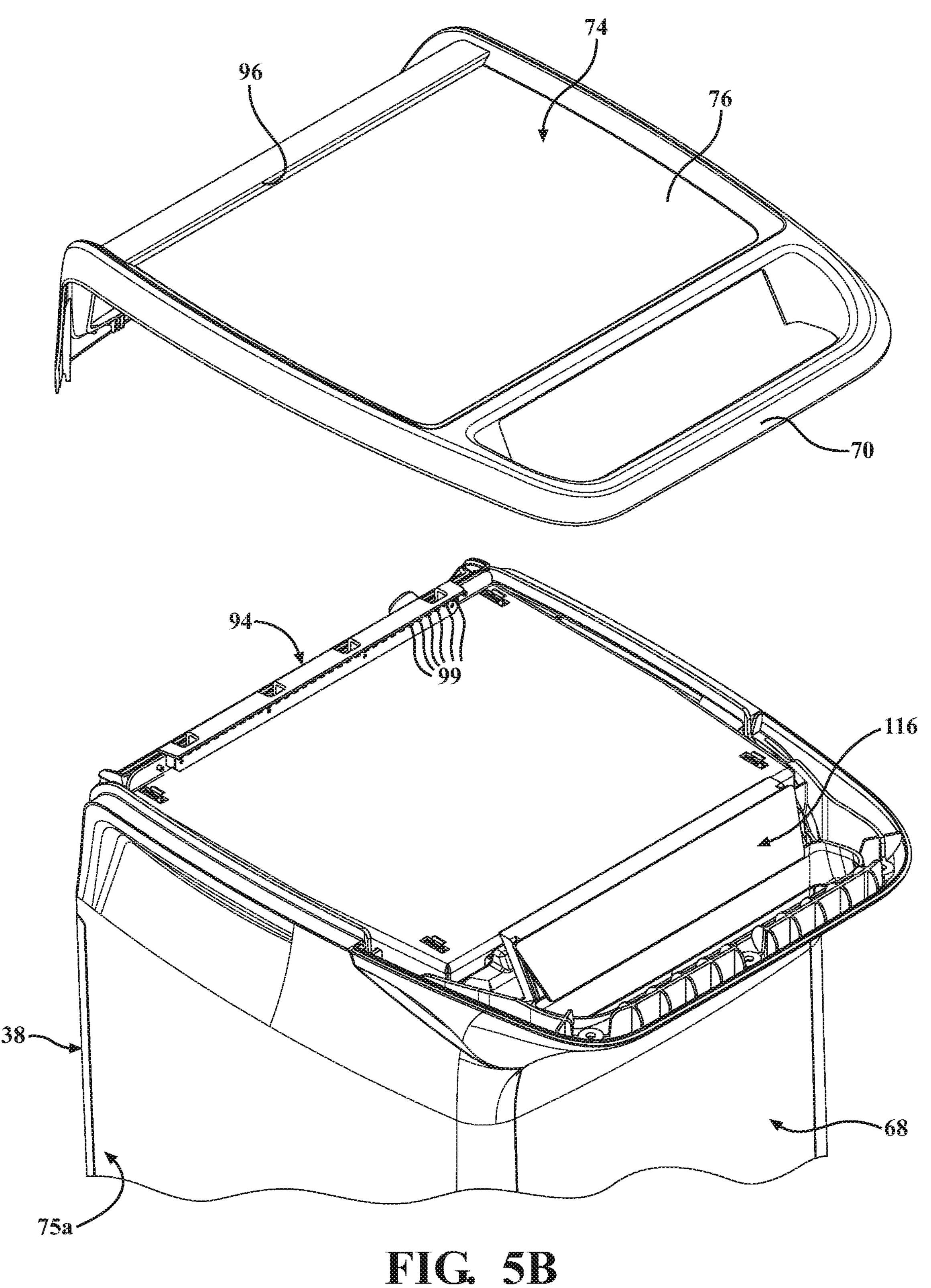
FIG. 5B is a perspective view of the waste collection cart assembly with the top portion of the housing exploded from the rest of the housing.

Referring to FIGS. 5A and 5B, the work surface 76 of the top portion 74 of the housing 38 may be set into the top portion 74 of the housing 38. The top portion 74 of the housing 38 may have a sidewall 96 at least partially surrounding the work surface 76. In some configurations, the sidewall 96 and the work surface 76 are integral or monolithic such that fluid spilled or otherwise disposed on the work surface 76 cannot leak into the interior of the housing 38. The top portion 74 of the housing 38 has an interior surface 98 opposite the work surface 76 and a thickness defined therebetween. The sidewall 98 has an outer surface facing the work surface 76, an inner surface facing the interior, and a thickness defined therebetween. In the configuration illustrated in FIG. 5A, the thickness of the sidewall 96 is less than the thickness between the work surface 76 and the interior surface 98 of the housing 38. In some configurations, the thickness of the work surface 76 is at least twice as thick as the thickness of the sidewall 96.

The light source assembly 94 may be disposed within the interior of the housing 38 and the sidewall 96 may be disposed between the light source assembly 94 and the work surface 76. More specifically, the light source assembly 94 may be configured to project light onto the inner surface of the sidewall 96. Due to the thickness of the sidewall and the material of the sidewall 96, light is configured to pass through the sidewall 96 and onto the work surface 76. The sidewall 96 may comprise a transparent material or a translucent material such that light projected from the light source assembly 94 passes through the sidewall 96 to illuminate the work surface 76. The light source assembly 94 illustrated in FIGS. 5A and 5B includes an array of light sources 99 arranged along the sidewall 96 such that light projected from the light sources 99 and through the sidewall 96 projects onto the work surface 76 to illuminate the work surface 76. In other configurations, the light source assembly 94 includes a single light source 99 disposed above the work surface 76. Each of the light sources 99 may comprise a light source selected from a light emitting diode, a bulb, a lamp, or another like device configured to emit visible light. In some configurations, portions of the housing 38 other than the sidewall 96 may not be transparent or translucent. Instead, the other portions of the housing 38 may be opaque to assist in the prevention of light being projected toward the monitor 95 in the procedure room.

Figure 9:
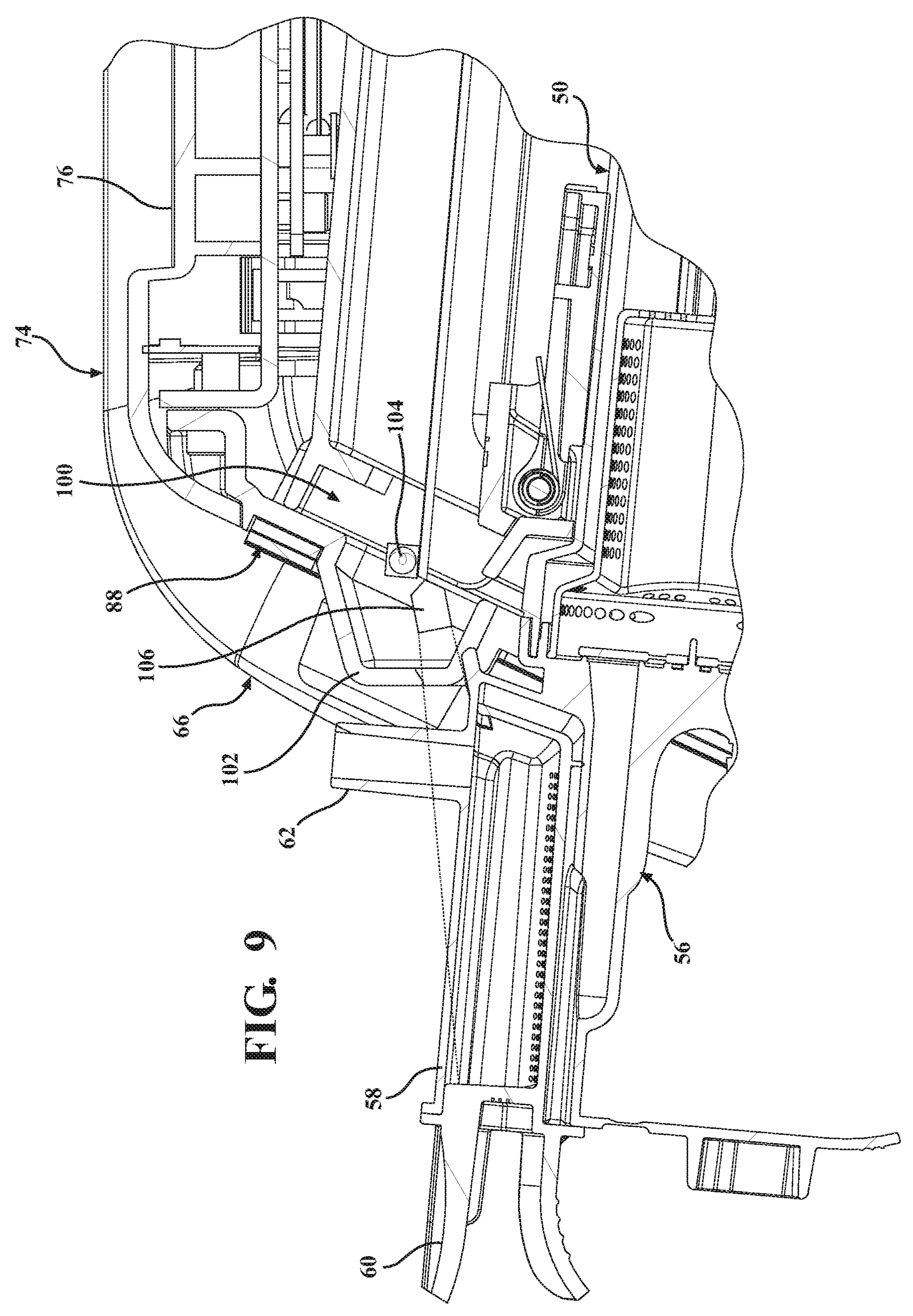
FIG. 9 is another sectional view of the waste collection cart assembly taken along line 7-7 of FIG. 3 illustrating a trap light assembly illuminating the specimen trap of the manifold.

In the configuration illustrated in FIGS. 8 and 9, a trap light assembly 100 may be coupled to the housing 38 adjacent the manifold receiver 50. The trap light assembly 100 may include a shroud 102 projecting outwardly from the exterior surface of the front portion 66 of the housing 38. More specifically, the shroud 102 may be disposed above the opening 54 of the manifold receiver 50. At least a portion of the manifold body 58 may comprise a transparent or translucent material such that contents of the specimen trap 60 may be visible with appropriate lighting when the specimen trap 60 is received in the manifold body 58. The trap light assembly 100 further comprises a light source 104 that may be coupled to the housing 38 and may be configured to project light beneath the shroud 102 and onto the specimen trap 60 to provide enhanced visibility of the specimen trap 60 during the medical procedure.

In one configuration the light projected is a low-intensity light. The shroud 102 is configured to limit light projecting away from the specimen trap 60 and to limit light being projected toward the monitor 95 in the procedure room when the front portion 66 of the housing 38 faces the patient/procedure site during the medical procedure. The light source 104 may comprise a light source selected from a light emitting diode, a bulb, a lamp, or another like device configured to emit visible light. To further limit the light projecting away from the specimen trap 60 in an unintended direction, the trap light assembly 100 may include a collimator 106 coupled to the housing 38 adjacent the light source 104. The collimator 106 is configured to focus the light projected from the light source 104 into collimated beams onto the specimen trap 60. As described above, in certain medical procedures it is important to mitigate any light projected toward the monitor 95 in the procedure room. Collimated light beams assist in focusing light projected toward the specimen trap 60 while mitigating diffraction of light that could project toward the monitor 95. In this manner, illumination of the specimen trap 60 may be accomplished without compromising the low lighting of the patient/procedure site. The collimator 106 may comprise one or more of a lens and a prism. An advantage of the configuration where the specimen trap 60 is illuminated while the waste material is being drawn into the waste container 40 is providing the user with greater visibility of the specimen trap 60 to discern whether a specimen has been collected.

Figure 25:
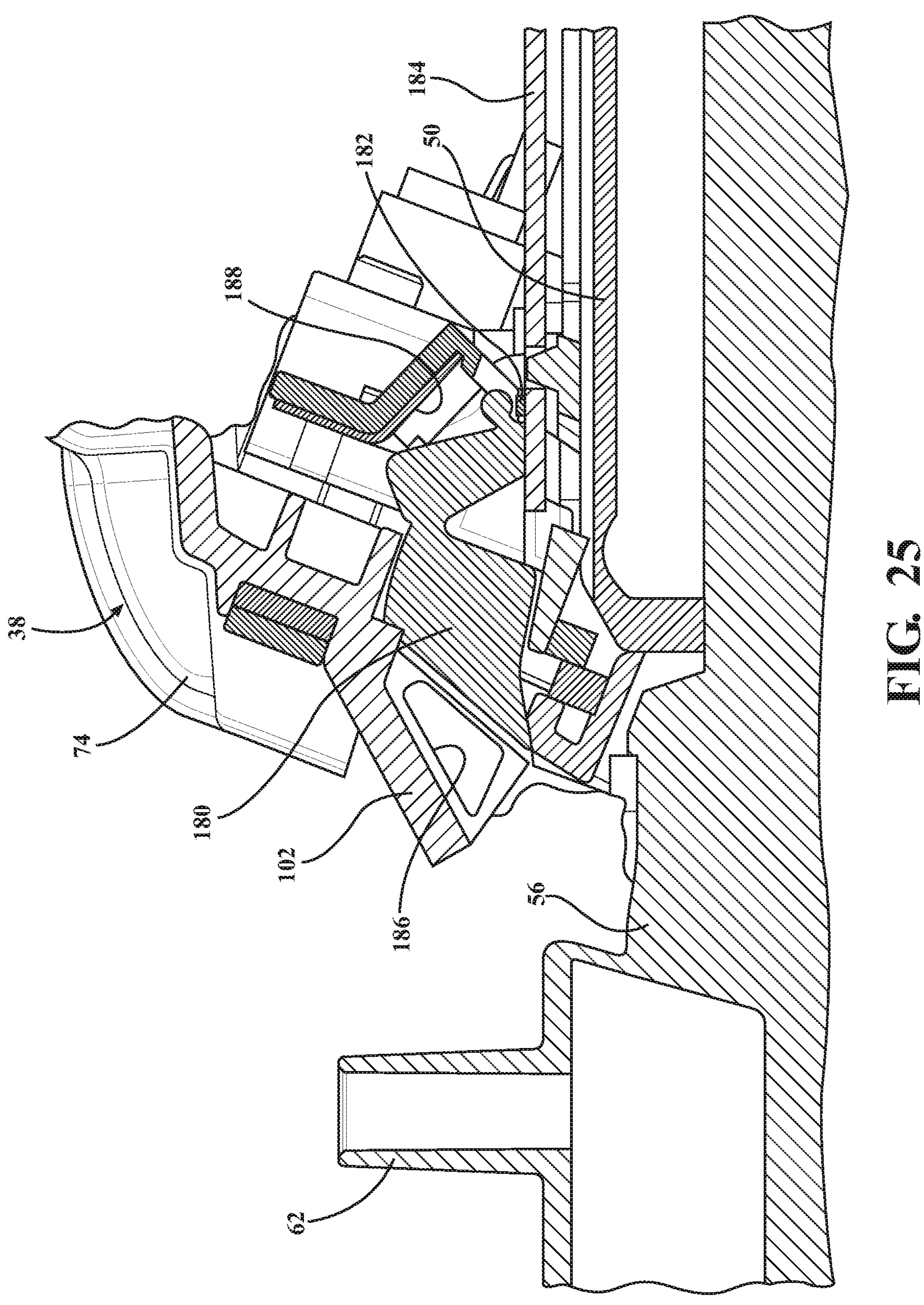
FIG. 25 is a sectional view of the waste collection cart assembly taken along line 25-25 of FIG. 6B.

In another configuration shown in FIG. 25, the shroud 102 projects from the exterior surface of the housing 38 adjacent the manifold receiver 50. More specifically, the shroud 102 may be disposed above the opening 54 of the manifold receiver 50. A light guide 180 may be coupled adjacent the manifold receiver 50 to direct light onto the specimen trap. More specifically, at least a distal end of the light guide 180 may be disposed adjacent the manifold receiver 50 to direct light onto the specimen trap to provide enhanced visibility of the specimen trap during the medical procedure. The shroud 102 may project distally from the exterior surface of the housing 38 at least 10 mm distal of the distal end of the light guide 180. In the illustrated configuration, distal is a direction away from the interior of the housing 38.

The shroud 102 may be configured to at least partially affect the light directed from the light guide 180. For instance, the shroud 102 may be configured to limit light projecting away from the specimen trap and to limit light being projected toward the monitor 95 in the procedure room when the front portion 66 of the housing 38 faces the patient/procedure site during the medical procedure (FIG. 14). In some configurations, the shroud 102 includes a first reflective surface facing the opening 54 of the manifold receiver 50. In some configurations, the shroud 102 is integral with the housing 38. In addition to partially affecting the light directed from the light guide 180, the shroud 102 may act to shield the light guide from being contacted by the user during a medical procedure.

In other configurations, a portion of the housing 38 extends distally relative to the distal end of the light guide 180 (not shown). Said differently, a portion of the housing 38 may hang over the light guide 180 to affect the diffraction of light from the light guide 180. In such a configuration, the portion of the housing 38 may extend distally of the distal end of the light guide 180 by at least 10 mm. Further, the portion of the housing 38 that extends distally relative to the distal end of the light guide 180 may include a reflective surface facing the opening 54 of the manifold receiver 50.

In the configuration illustrated in FIG. 25, the light guide 180 comprises a lens. The lens may comprise a silicone material or another compliant material. In other configurations the light guide 180 may comprise a fiber optic cable.

A light source 182 is configured to emit the light through the light guide 180. The light source 182 may be disposed in the interior of the housing 38. The light source 182 illustrated in FIG. 25 comprises a light emitting diode. In other configurations, the light source 182 may comprise a light source selected from a light emitting diode, a bulb, a lamp, or another like device configured to emit visible light. A printed circuit board 184 may be disposed within the housing 38 to control the flow of electricity to the light source 182. The light source 182 may be mounted to the printed circuit board 184 to assist in ease of assembly of the light source 182 in the interior of the housing 38.

In one exemplary configuration, the light source 182 is configured to emit light away from the opening 54 of the manifold receiver 50. The light may reflect off a second reflective surface 188 of the housing 38. The light may then be directed to the light guide 180. The light guide 180 may redirect the light toward the opening 54 of the manifold receiver 50 and onto the specimen trap 60. Some of the light from the light guide 180 may be directed to the first reflective surface 186 of the shroud 102 and then redirected onto the specimen trap 60.

Once the waste material either fills the waste container 40, or the user is otherwise prepared to dispose of the waste material, the waste collection cart assembly 30 may be transported by the user to a docking station 108 (shown in FIG. 15) or other disposal area. The waste material is emptied from the waste container 40 to a waste drain or treatment location, and the waste container 40 is cleaned for further use. Suitable construction and operation of the waste collection cart assembly 30 and the docking station 108 are disclosed in commonly owned U.S. Pat. No. 8,740,866, granted Jun. 3, 2014 and United States Patent Publication No. 2019/0001029 and U.S. Pat. No. 10,471,188, the entire contents of all are hereby incorporated by reference.

Figure 15:
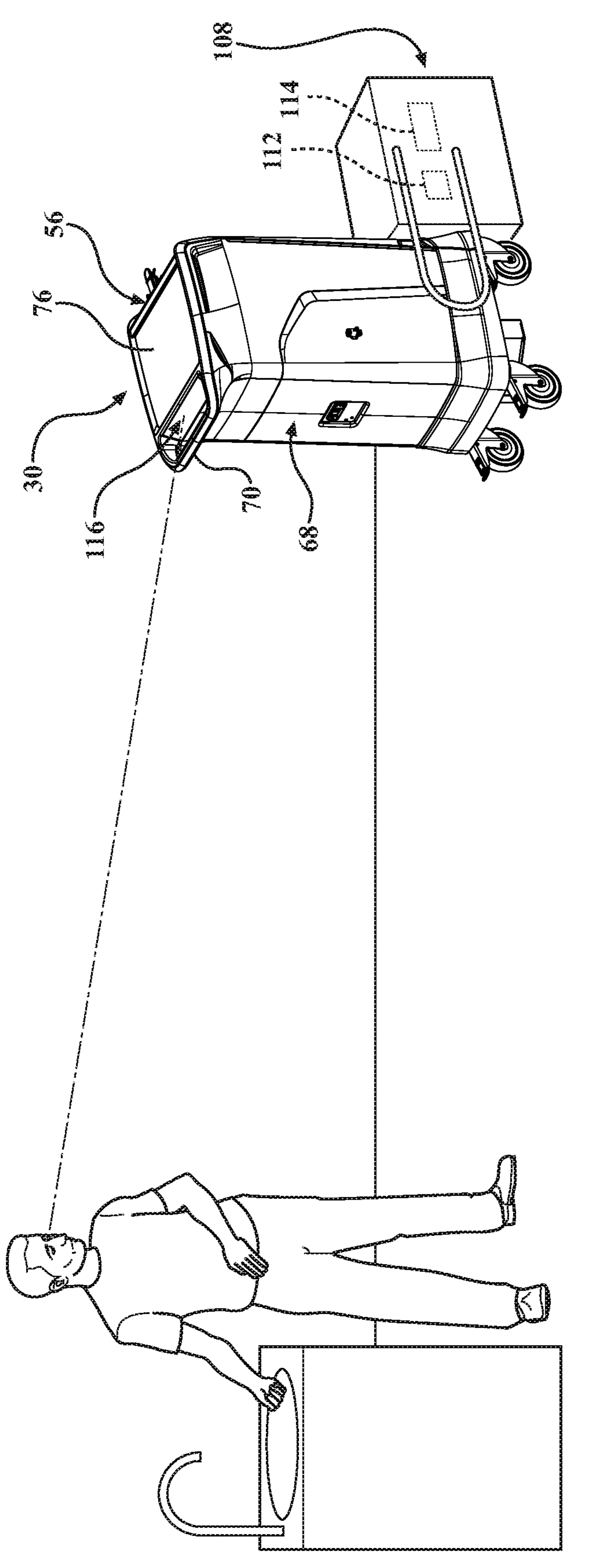
FIG. 15 is a perspective view of the waste collection cart assembly coupled to a docking station.

Referring to FIGS. 3 and 15, the chassis 36 comprises a docking coupler 110 (see FIG. 3) configured to dock the waste collection cart assembly 30 to the docking station 108 (see FIG. 15). When the docking coupler 110 is coupled to the docking station 108, the waste container 40 of the waste collection cart assembly 30 is configured to be in fluid communication with the docking station 108. The docking station 108 may comprise an off-load pump 112 and a docking controller 114, to generate signals to and receive signals from the off-load pump 112 to operate the off-load pump 112 to transfer waste material from the waste container 40 to the docking station 108. Both the off-load pump 112 and the docking controller 114 are shown schematically in FIG. 15.

The control panel 88 is further defined as a suction control panel 88 and the waste collection cart assembly 30 may comprise another control panel referred to as the docking control panel 116. The docking control panel 116 may be configured to generate signals to and receive signals from the cart controller 86. The cart controller 86 may be configured to generate signals to and receive signals from the docking controller 114 when the docking coupler 110 is coupled to the docking station 108. The docking control panel 116 may be coupled to the back portion 68 of the housing 38 adjacent the handle 70 such that the suction control panel 88 and docking control panel 116 are on opposite sides of the housing 38. The docking control panel 116 may comprise one or more knobs, dials, touch screen inputs, or the like, in communication with the docking controller 114, to allow the user to operate the off-load pump 112 of the docking station 108 to transfer waste material from the waste container 40 to the docking station 108 and to clean the waste container 40. While the docking control panel 116 is shown coupled to the back portion 68 of the housing 38, it is contemplated that the docking control panel 116 may be coupled to another portion of the housing 38.

While the suction control panel 88 is configured to generate signals to and receive signals from the cart controller 86 to operate one or both the vacuum regulator 48 and the vacuum pump 46, it is contemplated that the suction control panel 86 may additionally or alternatively generate signals to and receive signals from other sources (e.g., the docking controller 114). Similarly, while the docking control panel 116 is configured to generate signals to and receive signals from the docking controller 114 (via the cart controller 86) to operate the off-load pump 112 of the docking station 108, it is contemplated that the docking control panel 116 may additionally or alternatively generate signals to and receive signals from other sources. In other configurations, the suction control panel 88 may not be capable of generating signals to the docking controller 114. In such a configuration, the docking control panel 116 may have exclusive control over performance of docking operations (e.g., docking station coupling, cleaning, and waste material removal) and the suction control panel 88 may have exclusive control over performance of vacuum operations. Vacuum operations may include generating signals to the vacuum regulator 48 to operate the vacuum regulator 48 to adjust the vacuum level in the waste container 40 or in another manner as described above.

In some configurations, the waste collection cart assembly 30 may comprise a cleaning system to cooperate with the docking station 108 to clean and rinse the waste container 40 after emptying the waste container 40 of waste material. The cleaning system may be configured to generate signals to and receive signals from one or both the cart controller 86 and the docking controller 114. The docking control panel 116 may be configured to generate signals to and receive signals from one or both of the cart controller 86 and the docking controller 114 to operate the cleaning system. Suitable construction and operation of the cleaning system are disclosed in earlier identified United States Patent Publication No. 2019/0001029.

Figure 23:
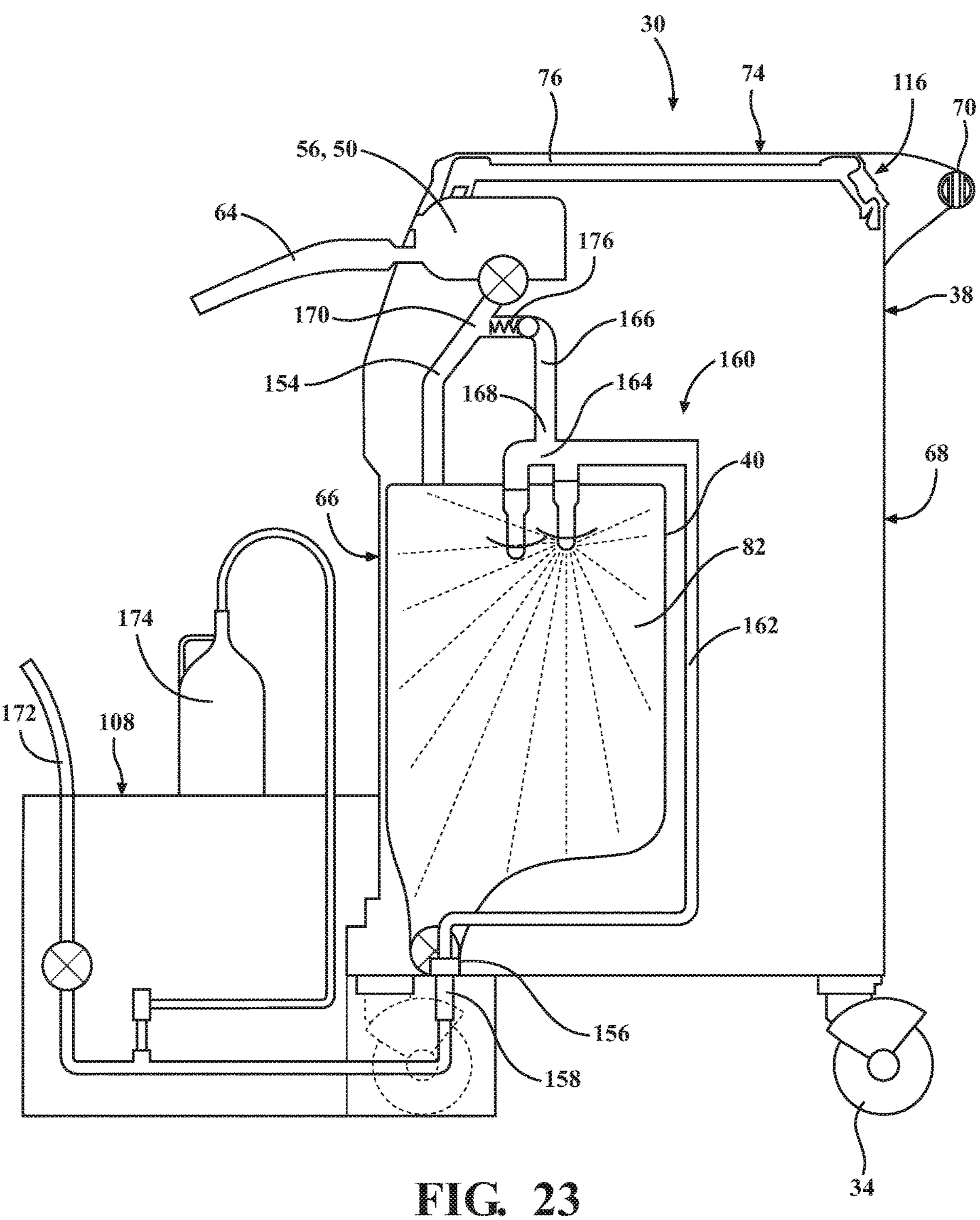
FIG. 23 is a schematic view of a cleaning system of the waste collection cart assembly.
Figure 24:
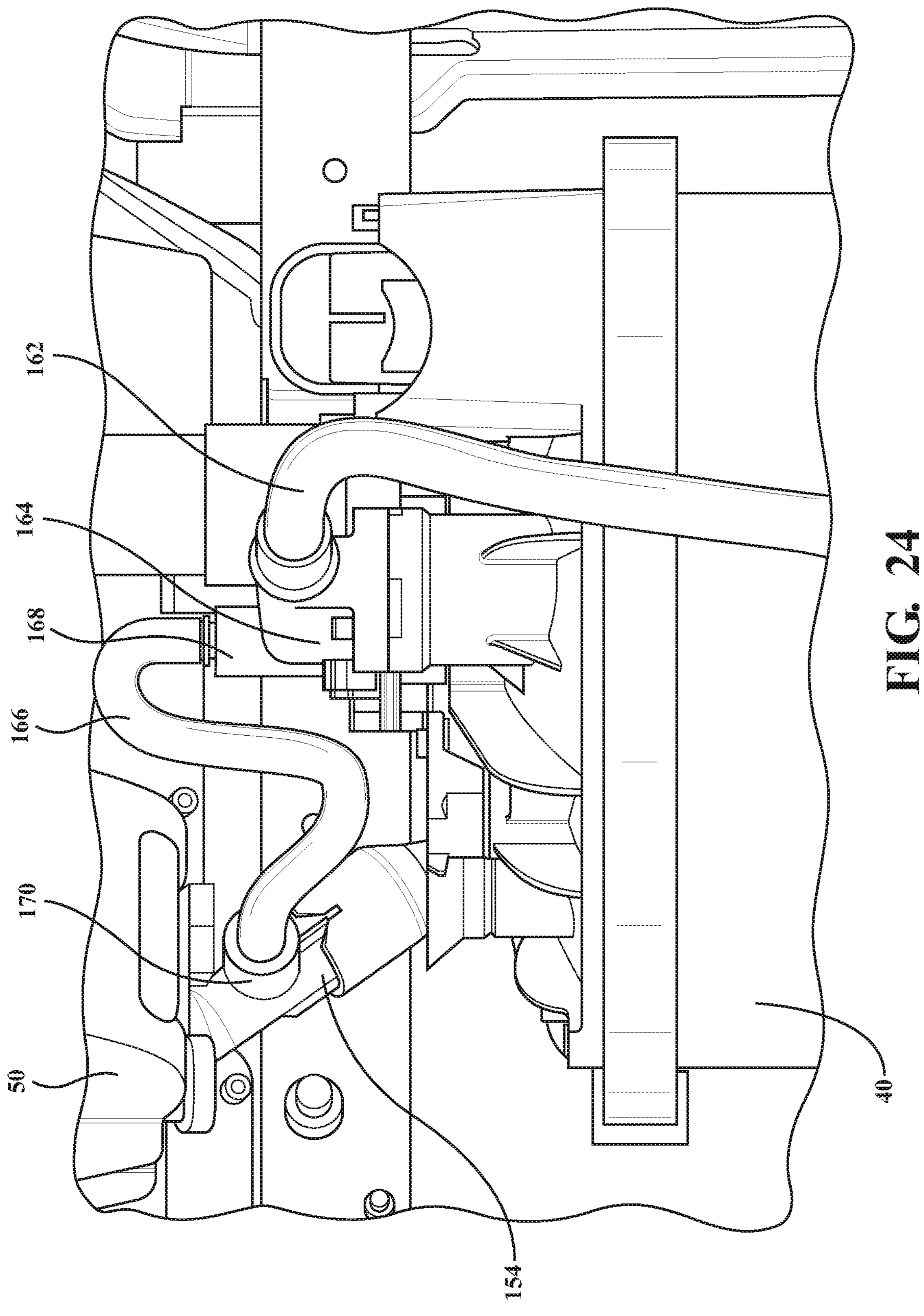
FIG. 24 is a partial perspective view of the cleaning system of the waste collection cart assembly.

Referring to FIGS. 23 and 24, one configuration of a cleaning system is illustrated. FIG. 23 illustrates a schematic cleaning system and FIG. 24 illustrates a portion of one configuration of the cleaning system. A drain line 154 may be coupled to the manifold receiver 50 and the waste container 40 for facilitating fluid communication between the waste container 40 and the manifold 56. More specifically, the drain line 154 directs waste material received from the manifold 56 and the suction line 64 from the manifold receiver 50 to the waste container 40. The waste collection cart assembly 30 may comprise a cart fluid coupler 156 configured to connect to a dock fluid coupler 158 of the docking station for permitting a transfer of a cleaning fluid from the docking station 108 to the waste collection cart assembly 30.

The waste collection cart assembly 30 may comprise a cleaning circuit 160. The cleaning circuit 160 may comprise a first cleaning line 162 coupled to the cart fluid coupler 156 and a nozzle 164. The first cleaning line 162 is configured to direct the cleaning fluid from the docking station 108 to the nozzle 164 when the cart fluid coupler 156 is connected to the dock fluid coupler 158 of the docking station 108. The nozzle 164 may be configured to direct cleaning fluid toward the waste chamber 82 of the waste container 40. The cleaning circuit 160 may comprise a second cleaning line 166 coupled to and in fluid communication with the nozzle 164 at a first junction 168. The second cleaning line 166 may be coupled to and in fluid communication with the drain line 154 at a second junction 170. The second junction 170 is disposed upstream of the waste container 40. The nozzle 164 may direct some of the cleaning fluid received from the first cleaning line 162 to the second cleaning line 166 and the nozzle 164 may direct the rest of the cleaning fluid into the waste chamber 82 of the waste container 40. The second cleaning line 166 may be configured to direct the cleaning fluid from the nozzle 164 to the drain line 154 to clean the drain line 154 when the cart fluid coupler 156 is connected to the dock fluid coupler 158 of the docking station 108. In other configurations, the second cleaning line 166 is coupled directly to the first cleaning line 162 at a junction and the first cleaning line 162 is configured to direct some of the cleaning fluid to the second cleaning line 166 and the rest of the cleaning fluid to the nozzle 164 and ultimately, into the waste chamber 82 of the waste container 40. In many configurations, the second cleaning line 166 is smaller in cross-sectional area than the first cleaning line 162 such that a majority of the cleaning fluid is directed toward the nozzle 164 and the waste container 40 instead of the drain line 154. After or during cleaning, the cleaning fluid received in the waste chamber 82 of the waste container 40 may be transferred back to the docking station 108 in the same manner as described above for transferring waste material from the waste container 40 to the docking station 108.

The cleaning fluid used in the cleaning system may comprise fresh water 172, a detergent 174, a mixture of fresh water and detergent, or a solution used to flush or clean the waste container 40 and lines 162, 166 or other components that are in fluid communication with the waste container 40.

In some configurations, the cleaning circuit 160 may comprise a check valve 176 disposed within the second cleaning line 166 between the first and second junctions 168, 170 to prevent waste material from the drain line 154 entering the first cleaning line 162. During operation of the vacuum source in a medical procedure, the check valve 176 is also configured to be closed to prevent waste material from entering the second cleaning line 166 and the nozzle 164 or first cleaning line 162.

Figure 11:
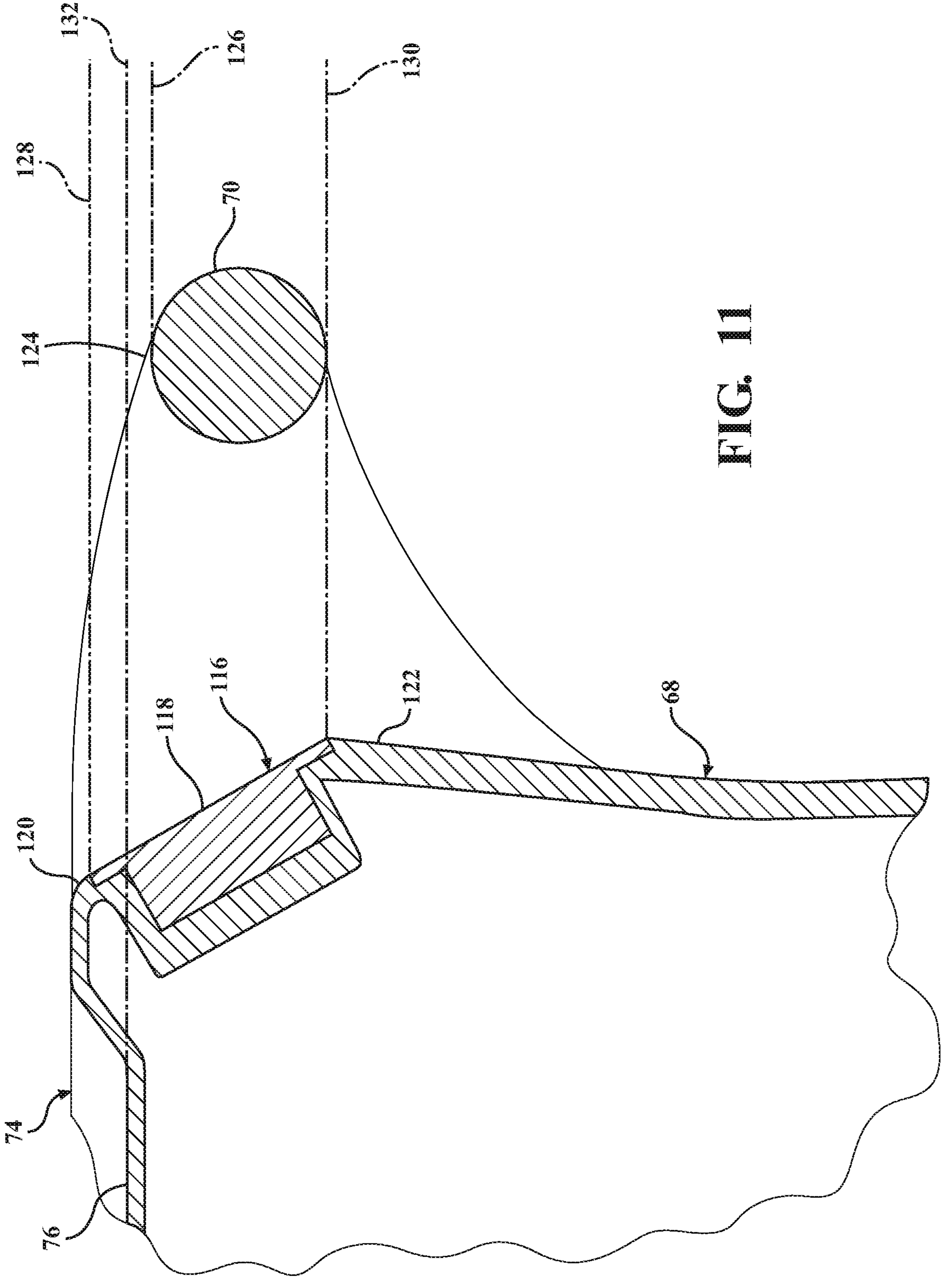
FIG. 11 is a sectional view of the waste collection cart assembly taken along lines 11-11 of FIG. 10.

In the configuration illustrated in FIGS. 10 and 11, the docking control panel 116 has a display 118 facing the grasping section 72 of the handle 70 to provide a graphical user interface to the user. The graphical user interface may display to the user a number of different indications relating to docking and cleaning procedures such as selection of a wash mode, abortion of a wash mode, whether the waste container has been emptied of waste material, the duration remaining before a wash mode will finish, release of the waste collection cart assembly 30 from the docking station 108, error notifications, etc. In some configurations, the display 118 outputs information to the user only i.e., the user may not be able to interact with the display to send signals to the cart controller 86. In other configurations the display 118 may be a touch screen and be configured to receive commends from the user via the graphical user interface.

The display 118 has a top edge 120 and a bottom edge 122. In one configuration, at least the top edge 120 of the display 118 is disposed above the grasping section 72 of the handle 70, but a substantial portion of the display 118 may also be disposed at a similar height above the floor surface as the work surface 76 and the handle 70. More specifically, in one configuration, a top-most portion 124 of the grasping section 72 of the handle 70 is disposed at a first height 126 above the floor surface. The top edge 120 of the display 118 of the docking control panel 116 is disposed at a second height 128 above the floor surface greater than the first height 126. The bottom edge 122 of the display 118 of the docking control panel 116 is disposed at a third height 130 above the floor surface less than the first height 126. The work surface 76 may be generally planar and parallel to the floor surface. The work surface 76 is disposed at a fourth height 132 above the floor surface greater than the third height 130 such that the bottom edge 122 of the display 118 of the docking control panel 116 is disposed below the work surface 76.

In another configuration, the fourth height 132 is less than the third height 130 such that the bottom edge 122 of the display 118 of the docking control panel 116 is disposed above the work surface 76. In still another configuration, both the second and third heights 128, 130 are greater than the first height 126 such that the top and bottom edges 120, 122 of the display 118 of the docking control panel 116 are disposed above the top-most portion 124 of the grasping section 72 of the handle 70.

Referring to FIG. 15, the positioning of the top edge 120 of the display 118 of the docking control panel 116 above the top-most portion 74 of the grasping section 72 of the handle 70 permits a user to view the display 118 from a distance. This may be advantageous to allow users to view a current state of the waste collection cart assembly 30 while the waste collection cart assembly 30 is coupled to the docking station 108. For instance, a user may be able to determine whether transfer of waste material from the waste container 40 to the docking station 108 is complete by viewing the display 118, which may display an indicator to the user that waste material has been transferred. Alternatively, the user may be able to determine time remaining for a particular wash mode to complete to put the waste collection cart assembly 30 in a ready-to-use state. Further, the positioning of the handle 70 at least partially surrounding the docking control panel 116 mitigates the possibility for inadvertent contact from the user or other objects to manipulate the docking control panel 116.

In the configuration illustrated in FIGS. 10 and 11, the display 118 of the docking control panel 116 may be planar and disposed at an oblique angle relative to the floor surface such that the display 118 faces away from the floor surface. In one configuration, the display 118 of the docking control panel 116 may be disposed at an angle of between 5 and 45 degrees from an axis that is perpendicular to the work surface 76 or the floor surface. In another configuration, the display 118 of the docking control panel 116 may be disposed at an angle of between 25 and 35 degrees from the axis that is perpendicular to the work surface 76 or the floor surface. The display 118 facing upwardly assists the user to view the docking control panel 116 from above the handle 70 and from a distance. The grasping section 72 of the handle 70 may be parallel to the display 118 of the docking control panel 116.

Figure 12:
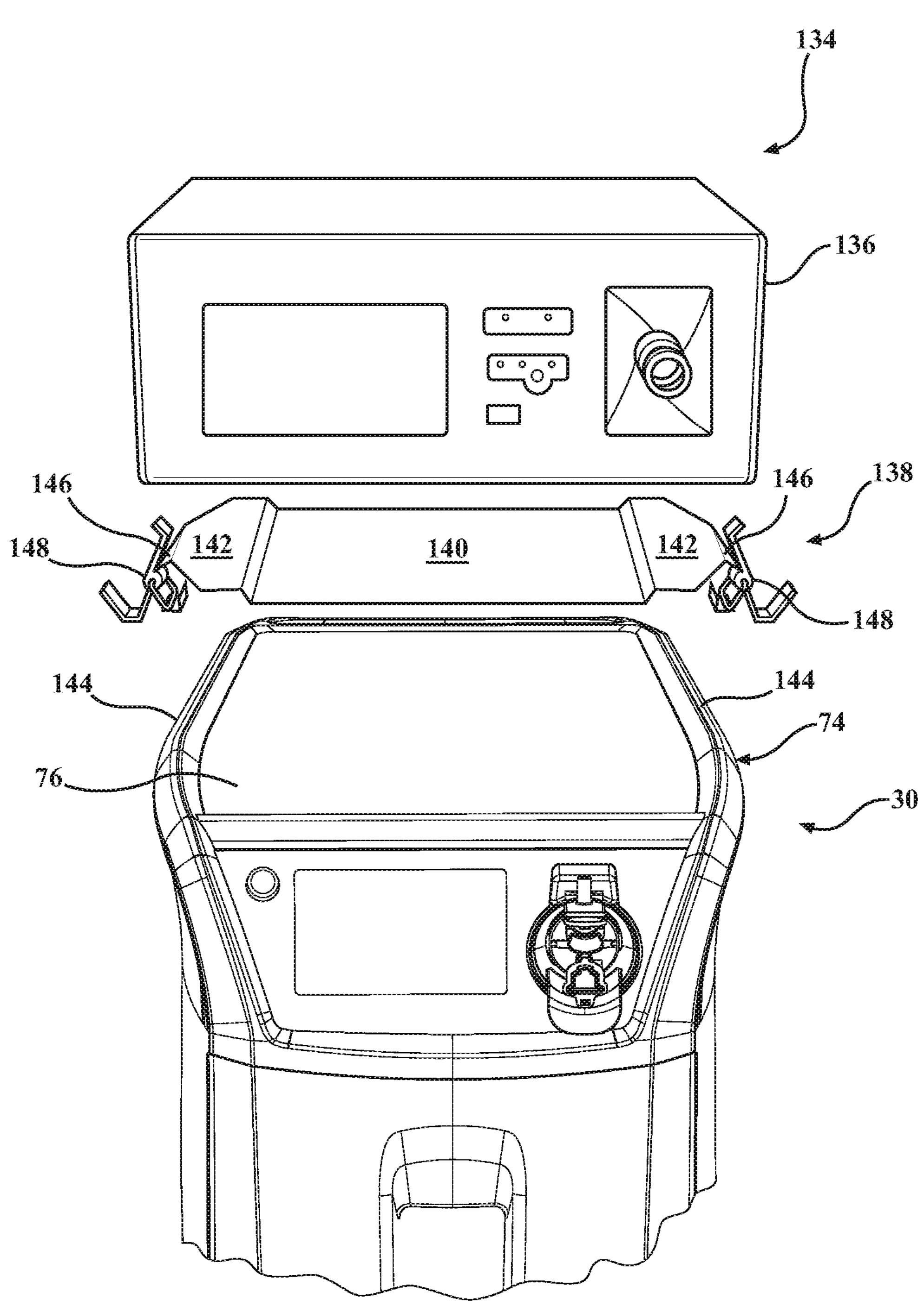
FIG. 12 is a partially exploded view of a smoke evacuation system and the waste collection cart assembly.
Figure 13:
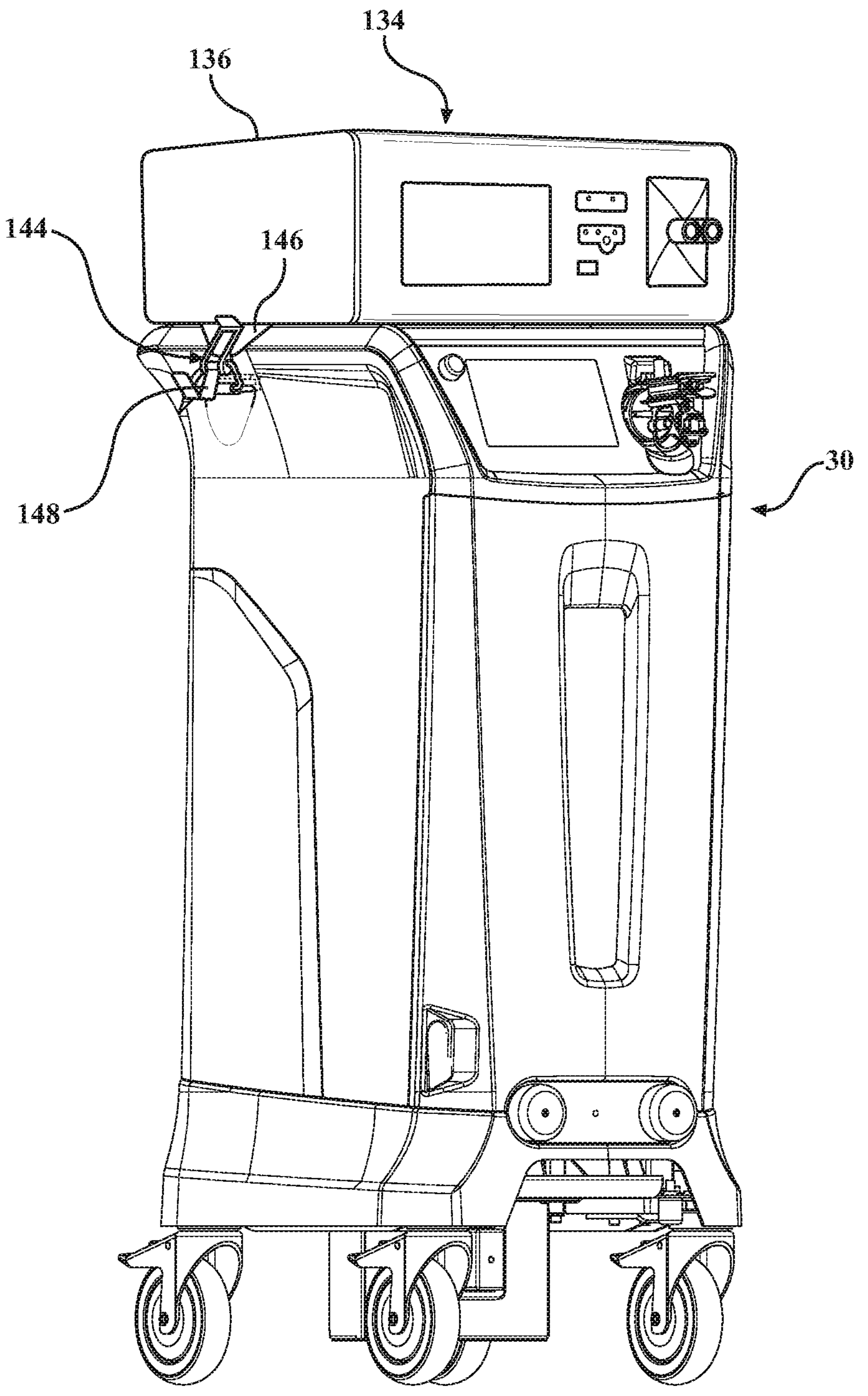
FIG. 13 is a perspective view of the smoke evacuation system coupled to the waste collection cart assembly.

Referring to FIGS. 12 and 13, a surgical console such as a smoke evacuation system 134 may be coupled to the waste collection cart assembly 30. The smoke evacuation system 134 may be utilized for removing smoke from a fluid, such as air, during a medical procedure. However, other uses for the smoke evacuation system 134 are evident to those skilled in the art. Suitable construction and operation of the smoke evacuation system is disclosed in commonly owned United States Patent Publication No. 2014/0338529, published Nov. 20, 2014, the entire contents of which are hereby incorporated by reference.

The smoke evacuation system 134 includes a smoke evacuation unit 136 and a bracket 138 for coupling the smoke evacuation unit 136 to the waste collection cart assembly 30. In the illustrated configuration, the bracket 138 may include a generally planar body portion 140 and one or more raised flange portions 142 extending from the body portion 140. The one or more flange portions 142 are configured to be coupled to the smoke evacuation unit 136. The smoke evacuation unit 136 may be coupled to the one or more flange portions 142 via fasteners. The body portion 140 is configured to be received by the inset work surface 76 described above. The top portion 74 of the housing 38 has one or more lips 144 at least partially surrounding the inset work surface 76. The bracket 138 further comprises wing portions 146 extending outwardly from the flange portions 142. The wing portions 146 may be shaped to complement the shape of the one or more lips 144 of the top portion 74 of the housing 38. The bracket 138 further includes couplers 148 attached to the wing portions 146 that are configured to couple the bracket 138 to the waste collection cart assembly 30. In one configuration, the couplers 148 comprise latches that are configured to grab onto the one or more lips 144 of the top portion of the housing 38. It is contemplated that the couplers 148 could instead be attached to the waste collection cart assembly 30 and the couplers 148 configured to grab onto the wing portions 146 of the bracket 138. While the bracket 138 is used to secure the smoke evacuation system to the waste collection cart assembly 30, it is contemplated that the bracket 138 may be used to secure other medical modules including other surgical consoles (e.g., an electrosurgical generator) or surgical equipment.

Another configuration for coupling medical modules to the waste collection cart assembly 30 is shown in FIGS. 19-22. A carrier assembly 200 that supports a medical module 202 may be coupled to the waste collection cart assembly 30 to secure the medical module 202 to the waste collection cart assembly 30. The carrier assembly 200 includes a carrier body 204 configured to be supported by an outer surface of the housing 38 of the waste collection cart assembly 30. In the configuration illustrated in FIGS. 19-22, carrier body 204 is configured to be supported by the work surface 76 of the top portion 74 of the housing 38 of the waste collection cart assembly 30.

In one configuration, the carrier body 204 may be integral with the medical module such that when the carrier body 204 is supported by the work surface 76, the medical module is as well. In other configurations, the carrier body 204 may be mounted to the medical module by a fastener to secure the carrier body 204 to the medical module. As will be appreciated from the description below. The carrier body 204 is typically configured to remain mounted to the medical module when the carrier assembly 200 is separated from the waste collection cart assembly 30. It is contemplated that the carrier body 204 may not remain mounted to the medical module when the carrier assembly 200 is separated from the waste collection cart assembly 30.

Figure 20:
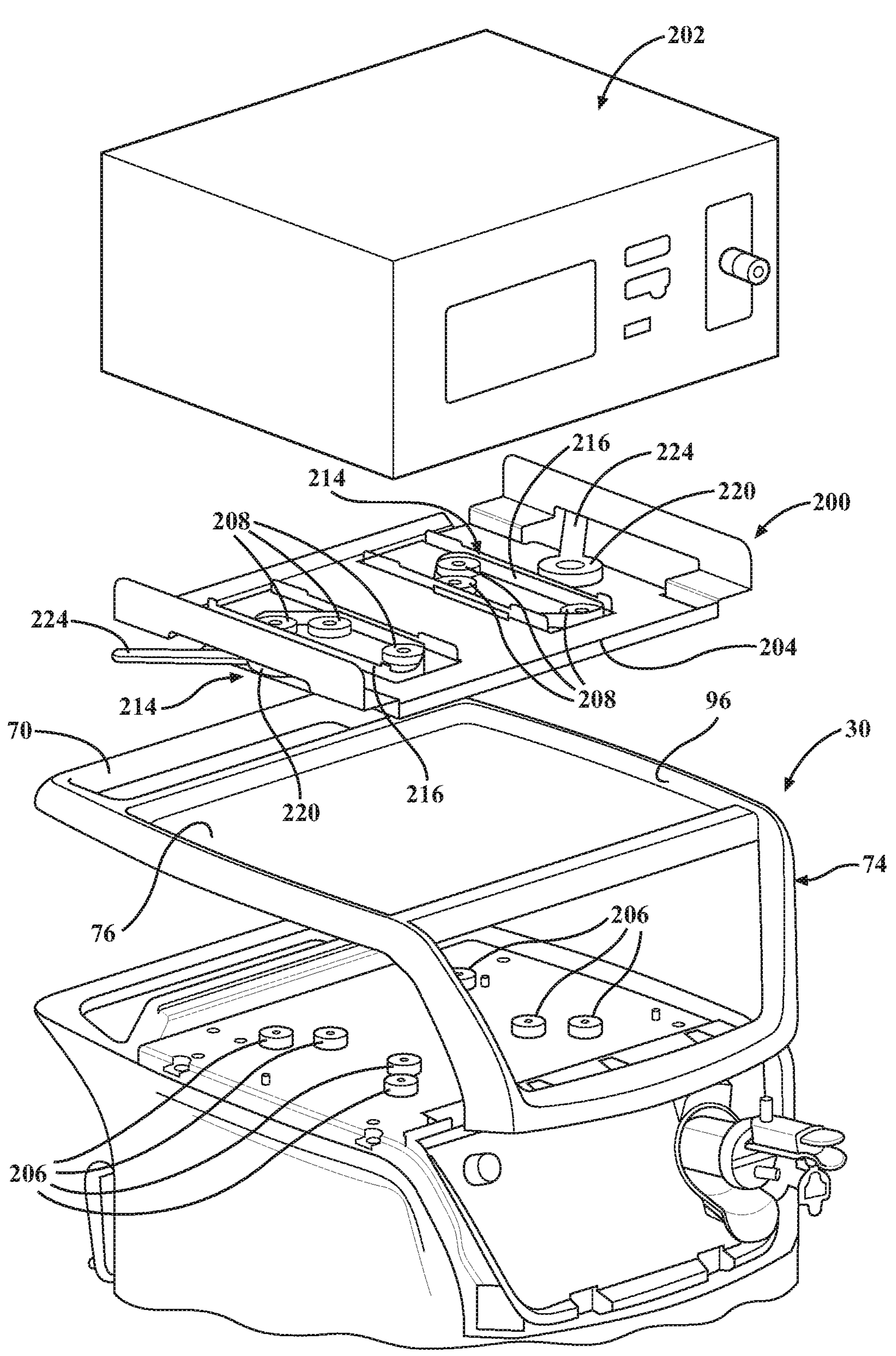
FIG. 20 is an exploded partial perspective view of the medical module, a carrier assembly, and the waste collection cart assembly.

Referring to FIG. 20, one or more first couplers 206 may be coupled to one or both the top portion 74 of the housing 38 and the chassis 36 disposed within the housing 38. The first coupler 206 is disposed beneath the work surface 76. For ease of description, a single first coupler 206 will be referenced hereafter. It is contemplated that two or more first couplers 206 may be employed to secure the medical module 202 to the waste collection cart assembly 30. In the illustrated configuration, the first coupler 206 is disposed beneath the top portion 74 of the housing 38. In other configurations, the first coupler 206 may be disposed within a thickness of the top portion 74 of the housing 38 defined between the work surface 76 and the interior surface 98 of the top portion 74 of the housing 38.

Figure 21:
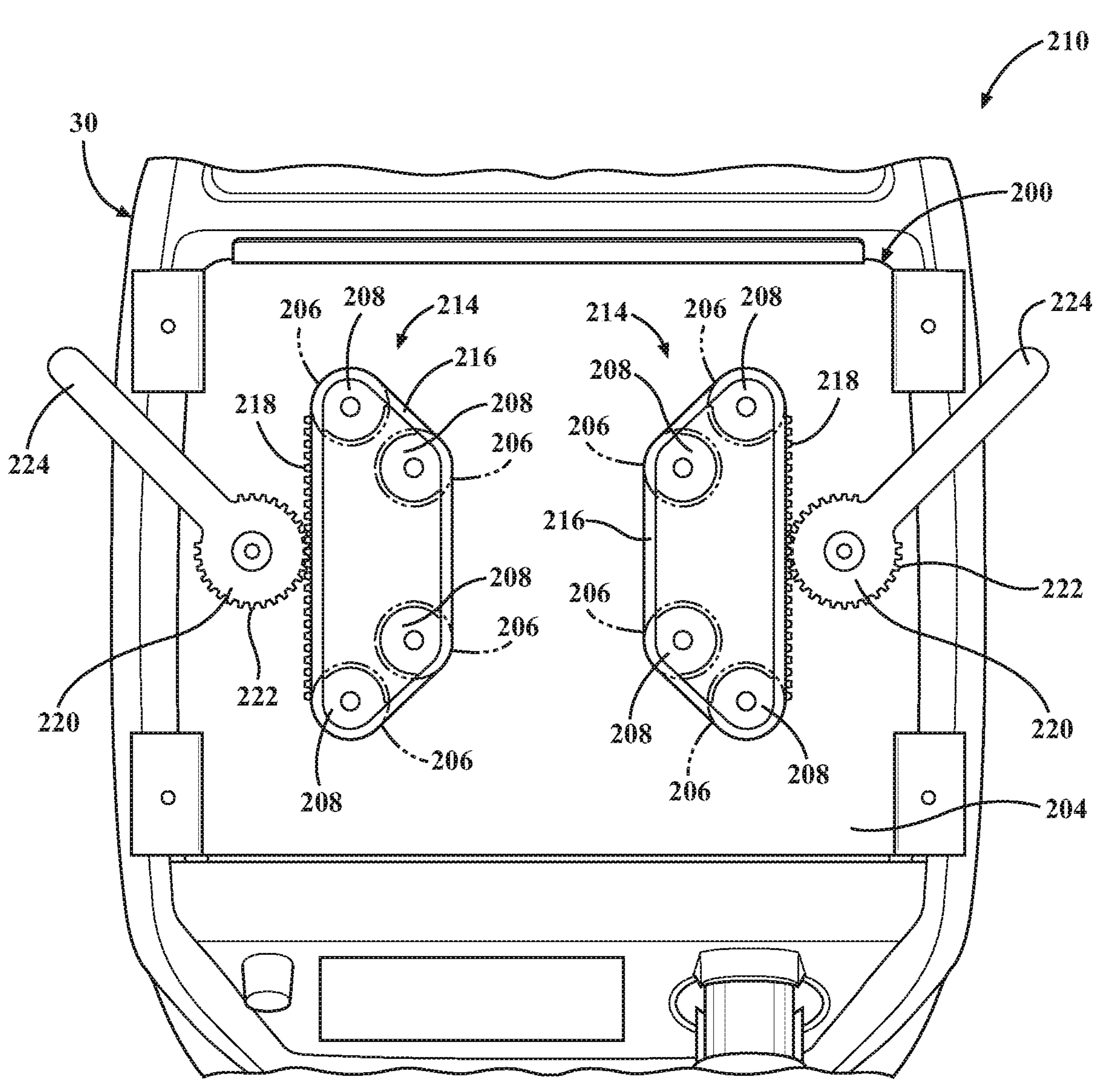
FIG. 21 is a plan view of the carrier assembly with an actuator in a first position.
Figure 22:
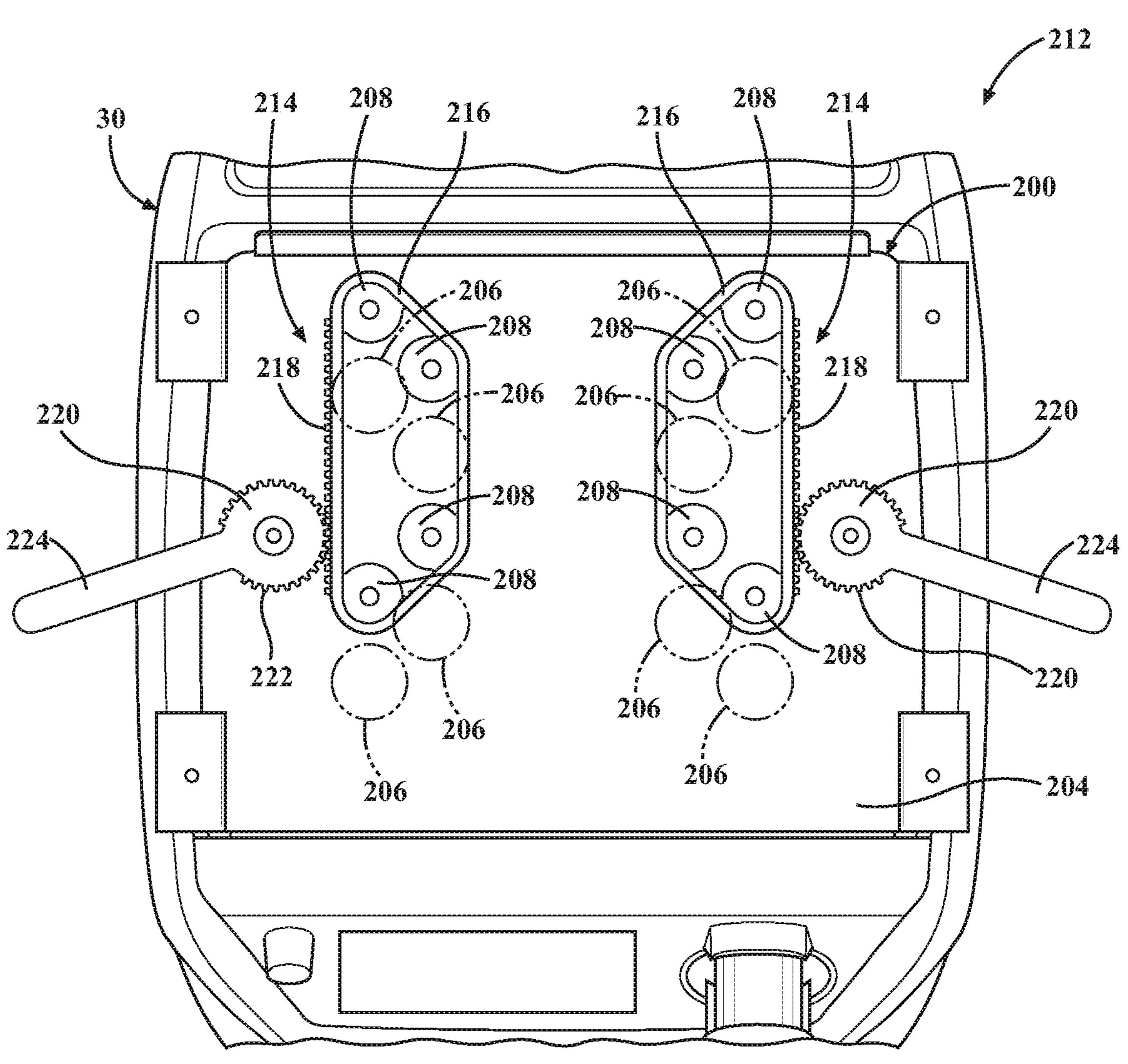
FIG. 22 is a plan view of the carrier assembly with the actuator in a second position.

Referring to FIGS. 21 and 22, the first coupler 206 is configured to be coupled to one or more second couplers 208 that are coupled to the carrier body 204. For ease of description, a single second coupler 208 will be referenced hereafter. It is contemplated that two or more second couplers 208 may be employed to secure the medical module 202 to the waste collection cart assembly 30. The first and second couplers 206, 208 are configured to move relative to each other to a first position 210 (FIG. 21) and a second position 212 (FIG. 22). The first and second couplers 206, 208 are aligned in the first position 210. In the first position 210, a magnetic attractive force between the first and second couplers 206, 208 is configured to secure the carrier body 204 of the carrier assembly 200 to the housing 38 of the waste collection cart assembly 30. The first and second couplers 206, 208 are misaligned in the second position 212. In the second position 212, a magnetic attraction between the first and second couplers 206, 208 is less than the magnetic attractive force between the first and second couplers 206, 208 in the first position 210. The reduced magnetic attraction between the first and second couplers 206, 208 permits the carrier body 204 of the carrier assembly 200 to be removed from the waste collection cart assembly 30.

In other configurations, the carrier body 204 is secured to the waste collection cart assembly 30 via electromagnetism. In such a configuration, the first and second couplers may be aligned when the carrier body 204 is supported by the waste collection cart assembly 30. An actuator (not shown) such as a switch may be configured to selectively supply current to one of the first and second couplers 206, 208 to create a magnetic field between the first and second couplers 206, 208 to secure the carrier body 204 and thus, the medical module to the waste collection cart assembly 30.

After certain medical procedures, it may be necessary to decontaminate portions of the waste collection cart assembly 30 and other associated tools and components that are exposed to the environment in a procedure room during a procedure. Decontaminating the interior of the housing 38 of the waste collection cart assembly 30 and components disposed within the interior can be difficult and time consuming. In some configurations, the interior of the housing 38 is further defined as an enclosed interior and establishes a decontamination barrier between the enclosed interior and the environment to obviate the need to clean interior surfaces of the housing 38 and the components disposed within the enclosed interior.

As described above, the housing 38 often comprises a plastic material. Plastic housings 38 may function well to enclose the interior of the housing 38. However, plastic housings 38 may lack the structural integrity to support the weight of certain medical modules 202. The plastic housing 38 may surround the chassis 36 such that the chassis 36 may reinforce the plastic housing 38 to support the weight of the medical module 202. Further, to secure the medical module 202 to the waste collection cart assembly 30 couplers such as clamps, clasps, or other fasteners may be employed. However, plastic housings 38 may not be rigid enough to engage these couplers. Instead, the couplers may need to engage the chassis 36 if the plastic housing 38 is not rigid enough to engage the couplers. The couplers may need to breach the decontamination barrier to engage the chassis 36. One advantage to using the first and second couplers 206, 208 that engage via magnetic attraction is that the first and second couplers 206, 208 may be secured together on opposite sides of the work surface 76 of the top portion 74 of the housing 38 while maintaining the decontamination barrier. Another advantage of disposing the first coupler 206 beneath the work surface 76 is to prevent fluid spilled or otherwise disposed on the work surface 76 from leaking into the interior of the housing 38. However, in alternative configurations, the first coupler 206 may not be disposed beneath the work surface 76, but is instead coupled to the housing 38 and projects upwardly from the work surface 76 of the housing 38.

In configurations where the first coupler 206 is disposed beneath the work surface 76 of the housing 38, the housing 38 may comprise a material that is permeable to magnetic fields. Said differently, the housing 38 comprises a material that would not disrupt magnetic attraction between the first coupler 206 and the second coupler 208 when the first and second couplers 206, 208 are aligned in the first position 210. One such material that is permeable to magnetic fields is plastic.

In one configuration, one of the first coupler 206 and the second coupler 208 comprises a magnetic material and the other of the first coupler 206 and the second coupler 208 comprises a ferromagnetic material. In certain circumstances it is advantageous for the first coupler 206 to comprise the ferromagnetic material so that when tools or equipment comprising ferromagnetic material other than the carrier assembly 200 are disposed on the work surface 76 of the top portion 74 of the housing 38, undesired magnetic attraction is eliminated. In other configurations, each of the first coupler 206 and the second coupler 208 comprise a magnetic material with oppositely arranged poles.

Referring to FIGS. 21 and 22, an actuator 214 may be coupled to the carrier body 204 of the carrier assembly 200 or one or both the housing 38 and the chassis 36 of the waste collection cart assembly 30 for moving one of the first and second couplers 206, 208 relative to the other of the first and second couplers 206, 208 to the first and second positions 210, 212. In the configurations illustrated in FIGS. 21 and 22, the actuator 214 is coupled to the carrier body 204 of the carrier assembly 200. The actuator 214 is configured to move the second coupler 208 relative to the first coupler 206 to the first and second positions 210, 212. In other configurations, the actuator 214 is coupled to one or both the housing 38 and the chassis 36 of the waste collection cart assembly 30. In FIGS. 21 and 22, two actuators 214 are illustrated. It is contemplated that a single actuator 214 may be used to secure the carrier body 204 to the waste collection cart assembly 30. It is also contemplated that three or more actuators 214 may be used to secure the carrier body 204 to the waste collection cart assembly 30.

The actuator 214 may comprise a sliding member 216 coupled to the second coupler 208. The sliding member 216 may be slidably coupled to the carrier body 204 of the carrier assembly 200. The sliding member 216 may be configured to move with the second coupler 208 relative to the first coupler 206 to the first and second positions 210, 212 such that actuation of the sliding member 216 moves the second coupler 208 to the first and second positions 210, 212. The sliding member 216 may have a plurality of rack teeth 218 disposed linearly along at least a partial length of the sliding member 216. The actuator 214 may further comprise a pinion 220 rotatably coupled to the carrier body 204 of the carrier assembly 200. The pinion 220 has a plurality of gear teeth 222 configured to engage the plurality of rack teeth 218 to move the sliding member 216 in response to rotation of the pinion 220. The actuator 214 may further comprise a lever 224 coupled to the pinion 220. The lever 224 may be configured to rotate the pinion 220 to engage the sliding member 216 for moving the sliding member 216 and the second coupler 208 relative to the first coupler 206 to the first and second positions 210, 212. While the actuator 214 illustrated in FIGS. 20-22 comprises the aforementioned rack and pinion design, it is contemplated that other actuators may be used to move the first and second couplers 206, 208 relative to each other to the first and second positions 210, 212. For instance, the actuator 214 may comprise a moveable member coupled to one of the first and second couplers 206, 208 and the moveable member moves relative to the other of the first and second couplers 206, 208 to the first and second positions 210, 212 in response to a user directly moving the moveable member. In another configuration, the actuator 214 comprises a rotatable member coupled to one of the first and second couplers 206, 208 and the rotatable member is configured to rotate one of the first and second couplers 206, 208 relative to the other of the first and second couplers 206, 208 to the first and second positions 210, 212.

In order for operation of the actuator 214 to be capable of moving the second coupler 208 in and out of alignment with the first coupler 206, the carrier body 204 must be located correctly to the housing 38 of the waste collection cart assembly 30. A visual indicator (not shown) may be used to indicate to a user where to dispose the carrier body 204 of the carrier assembly 200 relative to the housing 38 of the waste collection cart assembly 30 such that operation of the actuator 214 moves the second coupler 208 relative to the first coupler 206 to the first and second positions 210, 212. In one configuration, the visual indicator comprises an indicator selected from a marking, a label, and a score.

In other configurations, an alignment feature may be used to locate and/or indicate to a user where to dispose the carrier body 204 relative to the housing 38 of the waste collection cart assembly 30 so that operation of the actuator 214 is capable of aligning and misaligning the first and second couplers 206, 208 relative to each other to the first and second positions 210, 212. In the configuration illustrated in FIGS. 20-22, the alignment feature comprises the outer surface of the top portion 74 of the housing 38. Specifically, the carrier body 204 is configured to be placed on the inset work surface 76 of the top portion 74 of the housing 38. Further, the carrier body 204 is sized to fit in the recess defined by the inset work surface 76 and the surrounding sidewall 96. The carrier body 204 may be configured to abut the sidewall 96 to prevent the carrier body 204 from moving relative to the housing 38 of the waste collection cart assembly 30 when the actuator 214 is operated to move the second coupler 208 relative to the first coupler 206. In other configurations, one of the carrier body 204 of the carrier assembly 200 and the housing 38 of the waste collection cart assembly 30 comprises a protrusion or a surface defining a recess to engage the other of the carrier body 204 and the housing 38 to locate the carrier body 204 relative to the housing 38 and to prevent relative movement during operation of the actuator 214.

As with the bracket 138 above, the medical module 202 supported by the carrier assembly 200 may comprise a surgical console (e.g., an electrosurgical generator) or surgical equipment. Further, while the carrier assembly 200 described above is used in connection with a waste collection cart assembly 30, it is contemplated that the carrier assembly 200 may be used to secure medical equipment, surgical equipment, or other equipment to mobile carts other than waste collection cart assemblies 30.

It will be further appreciated that the terms "include," "includes," and "including" have the same meaning as the terms "comprise," "comprises," and "comprising." Moreover, it will be appreciated that terms such as "first," "second," "third," and the like are used herein to differentiate certain structural features and components for the non-limiting, illustrative purposes of clarity and consistency.

Several configurations have been discussed in the foregoing description. However, the configurations discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

The invention is intended to be defined in the independent claims, with specific features laid out in the dependent claims, wherein the subject matter of a claim dependent from one independent claim can also be implemented in connection with another independent claim.

The present disclosure also comprises the following clauses, with specific features laid out in dependent clauses, that may specifically be implemented as described in greater detail with reference to the configurations and drawings above.

I. A method for assisting a user to transfer a specimen during a medical procedure, said method comprising:
- providing a waste collection cart assembly having a waste container for collecting waste material, a manifold receiver coupled to the waste container and defining an opening, a vacuum source, and a housing to support the waste container, the manifold receiver, and the vacuum source;
- providing a manifold configured to be coupled to a suction line and the manifold receiver, with the manifold having a manifold body and a specimen trap positioned within the manifold body;
- inserting the manifold body into the opening of the manifold receiver;
- collecting the specimen in the specimen trap while the specimen trap is positioned within the manifold body and the manifold body is inserted in the opening of the manifold receiver;
- illuminating a work surface of the housing of the waste collection cart assembly that is disposed above the opening of the manifold receiver with a light source coupled to the waste collection cart assembly;
- providing a specimen container on the work surface of the housing such that the specimen container is illuminated;
- removing by the user the specimen trap having the specimen disposed therein from the manifold body while the manifold body is inserted in the opening of the manifold receiver; and
- transferring by the user the specimen from the specimen trap to the specimen container while the specimen container remains on the work surface.

II. A mobile medical cart system comprising:
- a mobile medical cart assembly comprising,
  - a frame,
  - a housing comprising a material that is permeable to magnetic fields, the housing coupled to and surrounding the frame, and the housing defining an enclosed interior to establish a decontamination barrier between the enclosed interior and the environment, and the housing having an outer surface facing away from the enclosed interior, and
  - a first coupler coupled to one of the frame and the housing, the first coupler being disposed beneath the outer surface; and
- a carrier assembly for securing medical equipment to the mobile medical cart assembly, the carrier assembly comprising,
  - a carrier body configured to be supported by the outer surface of the housing of the mobile medical cart assembly, and
  - a second coupler coupled to the carrier body;
- wherein one of the first and second couplers is configured to move relative to the other of the first and second couplers to a first position and a second position, and wherein the first and second couplers are aligned in the first position such that a magnetic attractive force between the first and second couplers is configured to secure the carrier body of the carrier assembly to the housing of the mobile medical cart assembly while maintaining the decontamination barrier, and wherein the first and second couplers are misaligned in the second position such that the magnetic attractive force between the first and second couplers in the second position is less than the magnetic attractive force between the first and second couplers in the first position to permit the carrier body of the carrier assembly to be removed from the medical cart assembly.

III. The mobile medical cart system of clause II, wherein one of the first coupler and the second coupler comprises a magnetic material and the other of the first coupler and the second coupler comprises a ferromagnetic material.

IV. The mobile medical cart system of clause II, wherein each of the first coupler and the second coupler comprises a magnetic material.

V. The mobile medical cart system of any of clauses II-IV, wherein one of the carrier assembly and the mobile medical cart assembly comprises an actuator for moving one of the first and second couplers relative to the other of the first and second couplers to the first and second positions.

VI. The mobile medical cart system of any of clauses II-IV, wherein the carrier assembly comprises the actuator, and wherein the actuator is configured to move the second coupler relative to the first coupler to the first and second positions.

VII. The mobile medical cart system of clause V, wherein the actuator comprises a sliding member coupled to one of the first and second couplers, the sliding member slidably coupled to one of the carrier body of the carrier assembly and the housing of the mobile medical cart assembly, and the sliding member configured to move with one of the first and second couplers relative to the other of the first and second couplers to the first and second positions such that actuation of the sliding member moves one of the first and second couplers to the first and second positions.

VIII. The mobile medical cart system of clause VII, wherein the sliding member has a plurality of rack teeth disposed linearly along at least a partial length of the sliding member, and wherein the actuator further comprises a pinion rotatably coupled to one of the housing of the mobile medical cart assembly and the carrier body of the carrier assembly, the pinion having a plurality of gear teeth configured to engage the plurality of rack teeth to move the sliding member in response to rotation of the pinion.

IX. The mobile medical cart system of clause VIII, wherein the actuator further comprises a lever coupled to the pinion and configured to rotate the pinion to engage the sliding member for moving the sliding member and one of the first and second couplers relative to the other of the first and second couplers to the first and second positions.

X. The mobile medical cart system of any of clauses V-IX, wherein one of the carrier body of the carrier assembly and the housing of the mobile medical cart assembly comprises a visual indicator to indicate to a user where to dispose the carrier body of the carrier assembly relative to the housing of the mobile medical cart assembly such that operation of the actuator moves one of the first and second couplers relative to the other of the first and second couplers to the first and second positions.

XI. The mobile medical cart system of clause X, wherein the visual indicator comprises a marking.

XII. The mobile medical cart system of any of clauses V-XI, wherein one of the carrier body of the carrier assembly and the housing of the mobile medical cart assembly comprises an alignment feature to indicate to a user where to dispose the carrier body of the carrier assembly relative to the housing of the mobile medical cart assembly such that operation of the actuator moves one of the first and second couplers relative to the other of the first and second couplers to the first and second positions.

XIII The mobile medical cart system of clause XII, wherein the alignment feature comprises one of a protrusion and a surface defining a recess.

XIV. The mobile medical cart system of clause XII, wherein the alignment feature comprises the outer surface of the housing of the mobile medical cart assembly defining a recess to receive the carrier body of the carrier assembly.

XV. The mobile medical cart system of clause XIV, wherein the outer surface has sidewall surrounding the recess and the carrier body of the carrier assembly is configured to abut the sidewall to prevent movement of the carrier body during operation of the actuator.

XVI. The mobile medical cart system of any of clauses II-XV, further comprising a medical module coupled to the carrier body of the carrier assembly to be secured to the mobile medical cart assembly.

XVII. The mobile medical cart system of clause XVI, wherein the medical module comprises a surgical console.

XVIII. A waste collection cart assembly for collecting waste material through a suction line and obtaining a specimen from the waste material via a specimen trap in a manifold during a medical procedure, the waste collection cart assembly comprising:

- a housing defining an interior;
- a waste container disposed within the interior of the housing and configured to be in fluid communication with the suction line and the manifold to collect the waste material during the medical procedure;
- a manifold receiver coupled to the waste container and having an internal surface defining an opening for receiving the manifold, the manifold receiver configured to facilitate fluid communication between the manifold and the waste container;
- a vacuum source configured to be in selective communication with the waste container for providing a vacuum on the waste container to draw the waste material from the suction line through the specimen trap, the manifold, and the manifold receiver into the waste container;
- a shroud projecting from a face of the housing, the shroud disposed adjacent the manifold receiver; and
- a light source disposed in the shroud.

XIX. A waste collection cart system for collecting a specimen from waste material through a suction line and for assisting a user in the transfer of the specimen to a specimen container, the waste collection cart system comprising:

- a manifold configured to be in fluid communication with the suction line, the manifold having a body defining an opening;
- a specimen trap that is configured to be removably received within the opening of the body of the manifold, the specimen trap configured to collect a specimen from the waste material when received by the body of the manifold; and
- a waste collection cart assembly comprising,
  - a waste container configured to be in fluid communication with the suction line and the manifold body to collect the waste material during the medical procedure,
  - a manifold receiver coupled to the waste container and having an internal surface defining an opening for receiving the manifold body, the manifold receiver configured to facilitate fluid communication between the manifold body and the waste container,
  - a vacuum source configured to be in selective communication with the waste container for providing a vacuum on the waste container to draw the waste material from the suction line through the specimen trap, the manifold body, and the manifold receiver into the waste container,
  - a housing coupled to the waste container, the vacuum source, and the manifold receiver, the housing having a first side adjacent the manifold receiver and a second side opposite the first side, and the housing having a work surface oriented to be generally parallel to a floor surface when the waste collection cart assembly is positioned on the floor, the work surface configured for supporting the specimen container, the work surface being disposed above the manifold receiver for ease of accessibility during the transfer of the specimen from the specimen trap to the specimen container, and
  - a light source assembly coupled to and disposed within the housing and configured to illuminate the work surface to provide enhanced visibility of a transfer of the specimen from the specimen trap to the specimen container.

XX. A waste collection cart assembly for collecting waste material through a suction line and a manifold, the waste collection cart assembly comprising:

- a housing defining an interior and having an external surface;
- a waste container disposed within the interior of the housing and configured to be in fluid communication with the suction line and the manifold to collect the waste material during the medical procedure;
- a manifold receiver coupled to the waste container and having an internal surface defining an opening for receiving the manifold, the manifold receiver configured to facilitate fluid communication between the manifold and the waste container;

a vacuum source configured to be in selective communication with the waste container for providing a vacuum on the waste container to draw the waste material from the suction line through the manifold and the manifold receiver into the waste container; and a line management member projecting outwardly from the housing and disposed adjacent the manifold receiver, with the line management member directing the suction line to the inlet fitting.

XXI. A carrier assembly for securing medical equipment to a housing or frame of a waste collection cart assembly having a first coupler, the carrier assembly comprising:

a carrier body configured to be supported by the housing or frame of the waste collection cart assembly;

a second coupler coupled to the carrier body, the second coupler configured to move relative to the first coupler to a first position and a second position, wherein the second coupler is configured to be aligned with the first coupler in the first position such that a magnetic attractive force between the first and second couplers is configured to secure the carrier body to the housing of the waste collection cart assembly, and wherein the second coupler is configured to be misaligned in the second position such that the magnetic attraction between the first and second couplers in the second position is less than the magnetic attractive force between the first and second couplers in the first position to permit the carrier body to be removed from the waste collection cart assembly; and an actuator coupled to the carrier body and the second coupler, the actuator configured to move the second coupler to the first and second positions.

XXII. A method of securing a medical module to a waste collection cart assembly, said method comprising:

providing a waste collection cart assembly having a housing defining an interior with a frame coupled to the housing and disposed at least partially within the interior, and a first coupler mounted to at least one of the housing and the frame;

providing a carrier assembly having a carrier body mounted to a medical module, and a second coupler movably coupled to the carrier body, and an actuator;

disposing the carrier body on an outer surface of the housing of the waste collection cart assembly;

moving the second coupler relative to the first coupler with the actuator from a misaligned position to an aligned positioned such that a magnetic attraction between the first and second couplers in the aligned position secures the carrier body and the medical module to the waste collection cart assembly.

What is claimed is:

1. A waste collection cart assembly for collecting waste material within a procedure room, the waste collection cart assembly comprising:

a housing comprising a top portion that is monolithic in construction, wherein the top portion includes a work surface, a front sidewall, and lips extending rearwardly from the front sidewall, wherein the work surface is inset from and surrounded by the front sidewall and the lips, wherein the front sidewall is formed from transparent or translucent material, wherein a thickness of the work surface is at least twice the thickness of the front sidewall to prevent light being projected through the work surface and to permit light to project through the front sidewall and to prevent the light from being projected toward the procedure room, and wherein the top portion of the housing, other than the front sidewall, is opaque;

a waste container supported on the housing;

a vacuum source supported on the housing and configured to provide a vacuum to draw the waste material from a suction line into the waste container; and a light source assembly disposed within the housing and positioned at least partially above the work surface that is opposite the front sidewall, wherein a thickness of the front sidewall is such that light from the light source assembly is configured to be projected through the transparent or translucent material of the front sidewall to illuminate the work surface, wherein the top portion other than the front sidewall being opaque is configured to prevent the light from being projected toward the procedure room.

2. The waste collection cart assembly of claim 1, wherein the light source assembly is disposed beneath an upper surface of the housing and adjacent the front sidewall.

3. The waste collection cart assembly of claim 1, wherein the top portion comprises side handles disposed on opposing sides of a front portion of the housing.

4. The waste collection cart assembly of claim 3, wherein the side handles extend from and are contoured to the lips.

5. The waste collection cart assembly of claim 3, further comprising a suction control panel disposed on the front portion of the housing and configured to receive inputs for controlling vacuum operations, wherein the suction control panel is disposed between the side handles.

6. The waste collection cart assembly of claim 5, further comprising a manifold receiver coupled to the front portion of the housing and configured to removably receive a manifold, wherein the light assembly is configured to project the light away rearwardly away from the manifold receiver.

7. The waste collection cart assembly of claim 6, wherein the manifold receiver is positioned between the suction control panel and one of the side handles.

8. The waste collection cart assembly of claim 6, further comprising a line management member projecting outwardly from the front portion of the housing adjacent the manifold receiver.

9. The waste collection cart assembly of claim 6, further comprising a trap light assembly comprising a shroud projecting outwardly from the front portion of the housing, and a light source positioned beneath the shroud and configured to project light towards the manifold receiver.

10. The waste collection cart assembly of claim 1, wherein the top portion further comprises a handle spaced apart from a back portion of the housing, and wherein the light assembly is oriented to project light rearwardly towards the handle.

11. The waste collection cart assembly of claim 10, further comprising a docking control panel configured to receive additional inputs for controlling docking operations, wherein the docking panel is disposed and coupled on the back portion of the housing and defined by a grasping section of the handle and an external surface of the back portion of the housing.

12. The waste collection cart assembly of claim 11, wherein a top edge of the docking control panel is positioned above the handle.

13. The waste collection cart assembly of claim 12, wherein the docking control panel is disposed at an oblique angle relative to the base of the waste collection cart assembly.

14. A waste collection cart assembly for collecting waste material within a procedure room, the waste collection cart assembly comprising:

a housing comprising a top portion that is monolithic in construction, wherein the top portion includes a work surface, a front sidewall, lips extending rearwardly from the front sidewall, and a handle spaced apart from a back portion of the housing, wherein the work surface is inset from and surrounded by the front sidewall and the lips, wherein the front sidewall is formed from transparent or translucent material, and wherein a thickness of the work surface is at least twice the thickness of the front sidewall to permit light to project through the front sidewall and to prevent light being projected through the work surface and configured to prevent the light from being projected toward the procedure room;

a waste container supported on the housing;

a vacuum source supported on the housing and configured to provide a vacuum to draw the waste material from a suction line into the waste container; and a light source assembly disposed within the housing and positioned at least partially above the work surface that is opposite the front sidewall, wherein the light source assembly is oriented to project light rearwardly through the transparent or translucent material of the front sidewall and towards the handle to illuminate the work surface.

15. The waste collection cart assembly of claim 14, further comprising a docking control panel configured to receive additional inputs for controlling docking operations, wherein the docking control panel is disposed and coupled on the back portion of the housing and defined by a grasping section of the handle and an external surface of the back portion of the housing.

16. The waste collection cart assembly of claim 15, wherein a top edge of the docking control panel is positioned above the handle.

17. The waste collection cart assembly of claim 16, wherein the docking control panel is disposed at an oblique angle relative to the base of the waste collection cart assembly.

18. A waste collection cart assembly for collecting waste material within a procedure room, the waste collection cart assembly comprising:

a housing comprising a top portion that is monolithic in construction, wherein the top portion includes a work surface, a front sidewall, lips extending rearwardly from the front sidewall, and side handles disposed on opposing sides of a front portion of the housing, wherein the work surface is inset from and surrounded by the front sidewall and the lips, wherein the front sidewall is formed from transparent or translucent material, and wherein a thickness of the work surface is at least twice the thickness of the front sidewall to permit light to project through the front sidewall and to prevent light being projected through the work surface and configured to prevent the light from being projected toward the procedure room;

a waste container supported on the housing;

a vacuum source supported on the housing and configured to provide a vacuum to draw the waste material from a suction line into the waste container;

a light source assembly disposed within the housing and positioned at least partially above the work surface that is opposite the front sidewall, wherein the light source assembly is configured to project light through the transparent or translucent material of the front sidewall; and a suction control panel disposed on the front portion of the housing and configured to receive inputs for controlling vacuum operations, wherein the suction control panel is disposed between the side handles.

19. The waste collection cart assembly of claim 18, further comprising a manifold receiver coupled to the front portion of the housing and configured to removably receive a manifold, wherein the manifold receiver is positioned between the suction control panel and one of the side handles.

* * * * *